United States Patent
Zhou et al.

(10) Patent No.: US 9,334,299 B2
(45) Date of Patent: May 10, 2016

(54) WATER-SOLUBLE CAMPTOTHECIN DERIVATIVE, PHARMACEUTICAL COMPOSITION AND USE THEREOF

(75) Inventors: Wenqiang Zhou, Changsha (CN); Jing Deng, Changsha (CN)

(73) Assignee: Hunan Fangshenghuamei Medical Tech. Co. Ltd., Changsha, Hunan (CN)

( * ) Notice: Subject to any disclaimer, the term of this patent is extended or adjusted under 35 U.S.C. 154(b) by 139 days.

(21) Appl. No.: 14/235,158

(22) PCT Filed: Jul. 27, 2011

(86) PCT No.: PCT/CN2011/077705
§ 371 (c)(1),
(2), (4) Date: Jan. 27, 2014

(87) PCT Pub. No.: WO2013/013404
PCT Pub. Date: Jan. 31, 2013

(65) Prior Publication Data
US 2014/0155336 A1 Jun. 5, 2014

(51) Int. Cl.
| | | |
|---|---|---|
| *C07H 15/26* | (2006.01) | |
| *A61K 31/706* | (2006.01) | |
| *C07H 11/04* | (2006.01) | |
| *A61K 31/7048* | (2006.01) | |
| *C07F 9/6561* | (2006.01) | |
| *C07H 19/10* | (2006.01) | |
| *C07H 19/207* | (2006.01) | |

(52) U.S. Cl.
CPC ............ *C07H 15/26* (2013.01); *A61K 31/7048* (2013.01); *C07F 9/6561* (2013.01); *C07F 9/65616* (2013.01); *C07H 11/04* (2013.01); *C07H 19/10* (2013.01); *C07H 19/207* (2013.01)

(58) Field of Classification Search
None
See application file for complete search history.

(56) References Cited

PUBLICATIONS

Pommier, Yves; Topoisomerase I Inhibitors: Camptothecins and Beyond; Nature Reviews/Cancer; Oct. 2006; pp. 789-802; vol. 6.
Thomas, Craig J., et al.; Camptothecin: Current Perspectives; Bioorganic & Medicinal Chemistry 12; 2004; pp. 1585-1604.
Verma, Rajeshwar et al.; Camptothecins: A SAR/QSAR Study; Chem. Rev. 2009; vol. 109; pp. 213-235.
Rahier, Nicolas J., et al.; Water-Soluble Camtothecin Derivatives that Are IntrinsicTopoisomerase I Poisons; Organic Letters; 2004; vol. 6, No. 3; pp. 321-324.
Wall, Monroe E., et al.; Plant antitumor agents. I. Isolation and structure of camptothecin, a novel alkaloidal leukemia and tumor inhibitor from Camptotheca acuminata; Journal of the Amecian Chemical Society (1966), 88(16), 3888-90 CODEN: JACSAT; ISSN: 0002-7863. English.

*Primary Examiner* — Eric Olson
(74) *Attorney, Agent, or Firm* — Yimei C. Hammond; Kremblas & Foster

(57) ABSTRACT

The present invention relates to a water soluble derivative of camptothecin and preparation method thereof, the derivative having a structure of formula I and being appropriate in water solubility, and having anti-cancer activity and stability of lactonic ring. The present invention also relates to a method for synthesizing the compound and medical use of the compound.

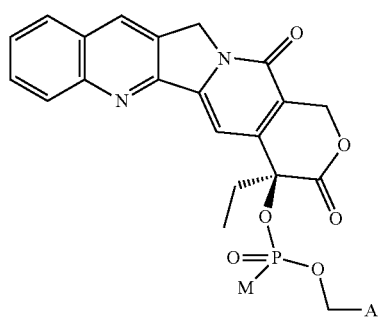

Formula I

20 Claims, 7 Drawing Sheets

Similar kinetics of cell killing observed in H146 cells as in H1693 (time- and dose dependent apoptotic cell death)

H146 SCLC
Cell Viability

H146 SCLC
Caspase activation

WATER-SOLUBLE CAMPTOTHECIN DERIVATIVE, PHARMACEUTICAL COMPOSITION AND USE THEREOF

FIELD OF THE INVENTION

The present invention relates to the field of pharmaceutics, particularly to the field of anticancer drugs, more particularly to pharmaceuticals of camptothecin derivatives.

BACKGROUND OF THE INVENTION

Camptothecin ("CPT") is a cytotoxic alkaloid first isolated and characterized by Wall and his coworkers (J. Am. Chem. Soc. 88, 3888, 1966) from leaves and barks of *Camptotheca accuminata* (Nyssaceae), a plant native to China. The primary cellular target for CPT is topoisomerase I (topo I), an enzyme involved in the relaxation of supercoiled chromosomal DNA during DNA replication by transient single-strand cleavage, unwinding, and reannealing of a DNA double helix. CPT binds at the interface of the covalent binary topo I-DNA complex to form stable ternary complex, which is prevents the reannealing or re-ligation, and consequently leads to replication-mediated double-strand breakage and DNA damage. Because CPT inhibition can lead to cell death during the S-phase of the cell cycle, CPT has been a focus of extensive studies in anticancer drug development (*Nature Review/Cancer*, October 2006 Vol. 6, pp 789-802; *Bioorg. Med. Chem.*, 2004, 12, pp 1585-1604).

The native CPT has a pentacyclic structure consisting of a fused ring system of quinoline rings (rings A and B), a pyrrolidine ring (ring C), an alpha-pyridone ring (ring D), and a six-membered lactone ring (ring E). CPT has only one asymmetric center at the 20-position and displays dextro-rotation due to the S-configuration of a tertiary hydroxyl group. At pH 7 or above, the lactone ring is hydrolyzed to give the carboxylate derivative, a hydrolysis process facilitated by the hydrogen bonding interaction between the 20(S)-OH and carbonyl groups in the E-ring. The instability of the E-ring, which is exacerbated at physiological conditions where the carboxylate derivative has preferential (150-fold higher) binding to human serum albumin, is a major limitation in the clinical applications of CPT as an anticancer chemotherapeutic agent. The carboxylate derivative of CPT is not only biologically inactive but also clinically very toxic. Another deficiency of CPT as a drug molecule is its poor water solubility. The native CPT is not soluble in water or in other aqueous vehicles that are suitable for parenteral administration. For reasons discussed above, it is not feasible to develop CPT to its water-soluble carboxylate derivative. Clearly, from the above discussion, improving physiological or in-vivo stability and water-solubility of the lactone ring of the CPT is the focus of the medicinal chemistry efforts in CPT-based anticancer drug development (*Bioorg. Med. Chem.*, 2004,12, pp 1585-1604; *Chem. Rev.*, 2009, 109(1), pp 213-235).

It is believed that the hydrolysis of the E-ring lactone is facilitated by the hydrogen bonding interaction between the 20(S)-hydroxyl group and the neighboring carbonyl group. Previous experiments have shown that replacing the 20(S)-hydroxyl group with other groups, e.g. Methyl, or protecting the 20(S)-hydroxyl group with functional groups, e.g. ester, could result in a stable E-ring lactone at physiological conditions. However, the 20(S)-hydroxyl group is essential for the pharmacological activity of camptothecin.

Such 20(S)-hydroxyl group protection would make the drugs difficult to exert anticancer activity in the human body.

The pro-drug strategy is a good approach to introduce ionizable functional groups to improve the water-solubility of the resulting pro-drug molecule. In such a case, the pro-drug approach can convert a water-insoluble CPT into a water-soluble CPT-pro-drug. Since the water-soluble CPT-pro-drug would be rapidly distributed through the body within a short period of time after being administered into the blood stream, the CPT-pro-drug would exist at a very low concentration at the time of degradation, preventing CPT from precipitation in blood stream. Obviously the pro-drug approach has the potential to bring in lactone stability, water-solubility, and convenient drug administration to facilitate the CPT anticancer drug development.

There have been reports to prepare pro-drugs of CPT and CPT-based compounds, mostly by esterification of the 20(S)-hydroxyl group to introduce various protecting functional groups, including lipophilic and ionizable functional groups (*Chem. Rev.*, 2009, 109(1), pp 213-235). Conversion of pro-drug esters to native CPT is mediated by a group of enzymes called esterases that are present in the blood of many animals, including humans. The weakness of the pro-drug esters is that the ester linkage is not very stable at the physiological condition in the human body, and is too easy to be broken by esterase, resulting in clinically unsatisfactory results for the CPT pro-drug esters. (*Chem. Rev.*, 2009, 109(1), pp 213-235). The CPT 20(S)-O-Phosphate or phosphonate monoesters have also been prepared to increase water-solubility and lactone in vivo stability. However, as shown in experimental results, the 20(S)-O-phosphate or phosphonate esters could not be converted to CPT at the physiological conditions, precluding their usage as pro-drugs of CPT (*Organic Lett.*, 2004, 6(3), pp. 321-324). The 20(S)-O-Phosphate or phosphonate monoester derivative of CPT does not have anticancer activities in itself.

Therefore, it is still desirable to discover a CPT pro-drug which has acceptable water solubility and acceptable enzymatic activity at the physiological conditions to liberate or promote the active component(s) or feature(s) of CPT.

SUMMARY OF THE INVENTION

One object of the present invention is to provide a novel CPT derivative with acceptable lactone stability and water solubility.

Another object of the present invention is to provide a novel CPT derivative, which can release an anti-cancer active component of CPT at physiological conditions.

Another object of the present invention is to provide a novel CPT derivative, which can release two anticancer active components including CPT at physiological conditions, to generate synergistic effects.

Another object of the present invention is to provide a method to prepare the above described 20(S)-O-nucleotide CPT derivative by the phosphoramidite ester chemistry.

A further object of the present invention is to provide an improved method of is treating certain forms of cancers.

To achieve the objects and in accordance with the purpose of the present invention, as embodiments and broadly described herein, the present invention relates to a compound of Formula I and pharmaceutically acceptable salts thereof,

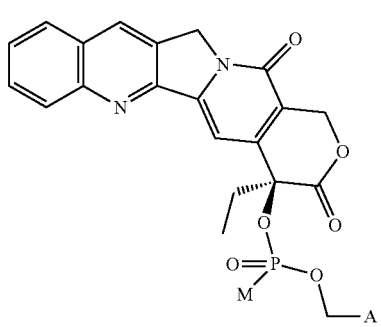

Formula I wherein M represents hydroxyl or thiol, A represents ribose or deoxyribose or ribose derivative, wherein A connects to phosphorus via oxygen of the hydroxyl group.

Preferably, the CPT derivative of the present invention has the chemical structure of Formula II,

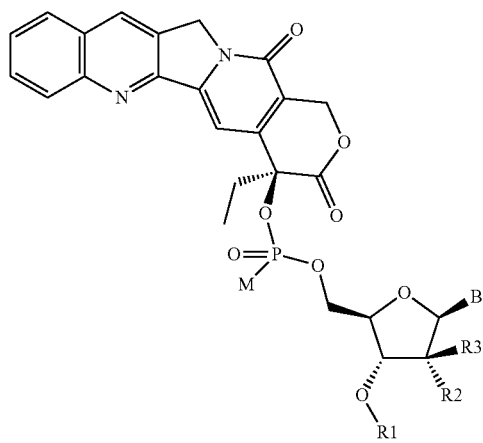

Formula II wherein M represents hydroxyl or thiol, R1 represents H, C1-C4 acyl, or an enzymatically reactive moiety;

R2 and R3 are the same or different, independently representing hydrogen, halo, hydroxyl, alkoxy, or an enzymatically reactive moiety;

B is hydrogen, optionally substituted thymine, optionally substituted adenine, optionally substituted cytosine, optionally substituted guanine, optionally substituted uracil, 5-fluorouricil, 5-aza-cytosine, 2-fluoroadenine, or 2-chloroadenine; or B is a heteroaryl or heteroalicyclic group other than adenine, thymine, cytosine or guanine and preferably has 1 to 3 mono-cyclic rings and 1 to 3 N, O or S atoms.

Preferably, B is a substituted thymine, substituted adenine, substituted uracil, substituted cytosine, or substituted guanine wherein the substitution group is one of the following groups: alkyl, aryl, heteroaryl or heteroalicyclic group, wherein the heteroaryl is or heteroalicyclic group has from 1 to 3 mono-cyclic or fused-rings and 1 to 3 N, O or S atoms.

In a preferred embodiment of the present invention, M is hydroxyl. In the following actual examples illustrating one or more embodiments of the present invention, unless specified, M is hydroxyl, as depicted in Formula II:

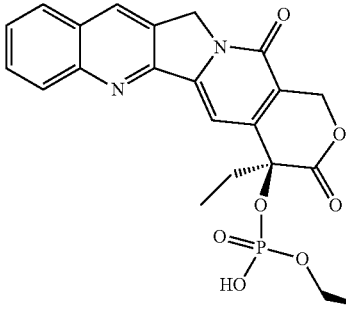

Formula II

In one embodiment, R1 is acyl, more preferably acetyl.

In another preferred embodiment, R1=R2=R3=H, B=hydrogen, thymine, adenine, cytosine, guanine, uracil, 5-fluorouricil, 5-aza-cytosine, 3,4,7,8-tetrahydroimidazo[1,3]diazepin-8-ol, 2-fluoroadenine, or 2-chloroadenine.

In another preferred embodiment, R1=R3=H, R2=OH, B=H, thymine, adenine, cytosine, guanine, uracil, or 5-aza-cytosine.

In another preferred embodiment, R1=Ac, R2=R3=H, B=H, thymine, adenine, cytosine, guanine, uracil, 5-aza-thymine, or 2-chloroadenine, wherein one hydrogen of the amino group is substituted by acetyl.

In another preferred embodiment, R1=Ac, R2=F, R3=H, B=2-chloroadenine, wherein one hydrogen of the amino group is substituted by acetyl.

In another preferred embodiment, R1=Ac, R2=H, R3=OAc, B=2-fluroadenine, wherein one hydrogen of the amino group is substituted by acetyl.

In another preferred embodiment, R1=Ac, R3=H, R2=OAc, B=H, thymine, adenine, cytosine, guanine, uracil, or 5-aza-thymine, wherein one hydrogen of the amino group is substituted by acetyl.

The present invention also relates to a method for treating malignant tumors or cancer in a mammal, comprising administering an effective amount of a composition containing one or more of the compounds comprising Formula I depicted above.

The camptothecin derivatives of the present invention not only have water solubility suitable for drug administration and delivery in the body, but also have enhanced stability for the lactone ring of camptothecin and reduced drug toxicity.

Additional objectives and advantages of the present invention will be set forth in part in the following detailed description, and in part will be obvious and inherent from the description, or may be achieved through applications of the present invention.

DETAILED DESCRIPTION OF THE INVENTION

Figure 1:
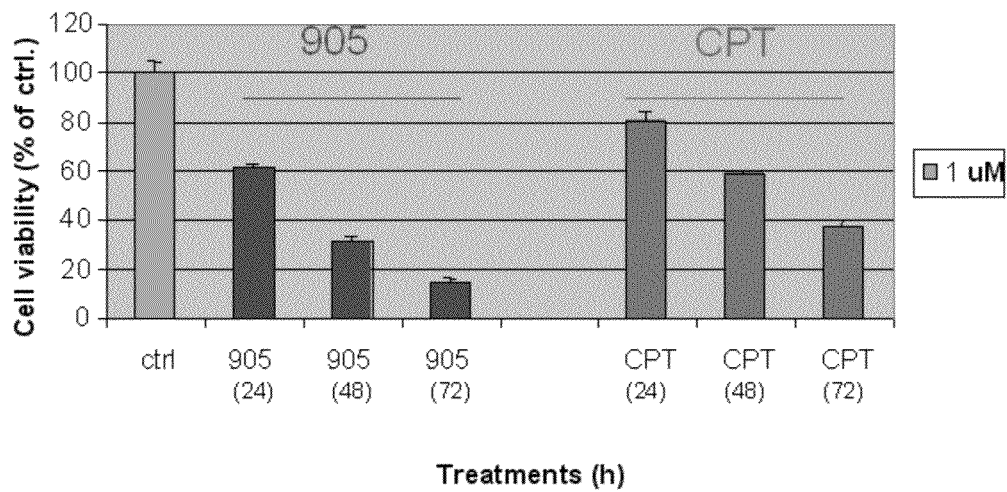
FIG. 1. Dix-905 triggered cell killing response better than that of CPT in H1693 cells.

The term "ribose derivative" refers to a derivative having a backbone of ribose or deoxyribose, in which one or more hydrogens bonded to carbon members in the ring, or one or more hydrogens from the hydroxyl group are substituted by other groups. The other groups herein are selected from the group consisting of alkenyl, alkynyl, alkoxyl, cycloalkyl, cycloalkeynyl, acyl, acylamino, acyloxyl, amino, aminocarbonyl, alkoxycarbonylamino, azide, cyano, halogen, hydroxyl, keto, thiocarbonyl, carboxyl, carboxyalkyl, arylthio, heteroarylthio, heterocyclic thiol, thiol, alkylthio, aryl, aryloxyl, heteroaryl, aminosulfonyl, aminocarbonyl amino, heteroaryloxyl, heterocyclic, heterocycloxyl, hydroxamino, alkoxylamino, nitro, —SO-alkyl, —SO-aryl, —SO-heteroaryl, —SO₂-alkyl, —SO₂-aryl, —SO₂-heteroaryl, nucleobase, and nucleobase analogs.

Unless specifically indicated, the term "nucleobase" has its normal biologic meaning, including purines and pyrimidines, e.g., adenine, guanine, thymine, cytosine, or uracil.

The term "nucleobase analog" refers to a nucleobase having 1 to 3 mono-cyclic rings and 1 to 3 N, O or S atoms, of which the ring backbone is different from that of adenine, thymine, cytosine or uracil, preferably a mono-cyclic or twofused heteroarene. Examples of monocyclic heteroarene include pyrrole, imidazole, pyrazole, pyridine, pyrazine, pyrimidine, pyridazine, indolizine, isoindole, indole, furan, [1,2,4]Oxadiazole, [1,3,4]Oxadiazole, [1,2,4]thiadiazole, [1,3,4]thiadiazole. Examples of 2-fused heteroarene include indazole, quinazine, isoquinaline, quinoline, phthalazine, naphthylpyridine, quinoxaline, quinolizine. Examples of Mono-ring and two-fused heteroalicyclic hydrocarbon include completely or partially hydrogenated products of the compounds listed above. The term "nucleoside" refers to a glycoside or glucoside formed by a nucleobase attaching to the C-1' of a ribose or deoxyribose, including ribonucleoside and deoxyribonucleoside.

The term "nucleoside analog" refers to a nucleoside derivative in which one or more hydrogens in carbon-hydrogen bonds, nitrogen-hydrogen bonds, or hydroxyl is groups of the pentose moiety and/or the nucleobase are substituted, or a nucleobase analog has the following features: a heteroaryl or heteroalicyclic group other than adenine, thymine, cytosine or guanine, having 1 to 3 mono-rings and 1 to 3 N, O or S atoms.

The term "alkyl" refers to a branched or unbranched and saturated hydrocarbon chain with 1-5 carbon atoms, such as methyl, ethyl, n-propyl, isopropyl, n-butyl, isobutyl and tert-butyl.

The term "alkoxyl" refers to R—O—, in which R is the alkyl defined above, optionally substituted by halo, hydroxyl or amino. Examples of alkoxyls include, but are not limited to, methoxyl, ethoxyl, n-propoxyl, iso-propoxyl, n-butoxyl, tert-butoxyl, sec-butoxy, n-pentyloxy, 1-methybutoxy, 2-methylbutoxy, 3-methylbutoxy, neopentyloxy, trifluromethyloxy, etc.

The "aryl" refers to a C6-C18 aromatic ring group, having a mono-cyclic ring (e.g. phenyl), multi-rings (e.g., biphenyl) or fused-rings(e.g., naphthyl and anthryl). Preferred aryl includes phenyl and naphthyl etc..

Term "heteroaryl" refers to a group derived from an aromatic (i.e. fully unsaturated) group, having 1, 2, 3, 4, 5, 6, 7, 8, 9, 10, 11, 12, 13, 14 or 15 carbon atoms, and 1, 2, 3 or 4 ring members of at least one ring are selected from O, N and S atoms. The heteroaryl group may have a mono-cyclic ring group (e.g., pyridyl or furyl) or fused-ring (e.g., indolizinyl, benzothiazolyl or benzothienyl). Examples of heteroaryl include, but are not limited to, [1,2,4]oxadiazole, [1,3,4]oxadiazole, [1,2,4]thiadiazole, [1,3,4]thiadiazole, pyrrole, imidazole, pyrazol, pyridine, pyrazine, pyrimidine, pyridazine, indolizine, isoindole, indole, indazole, purine, quinolizidine, isoquinoline, quinoline, phthalazine, naphthylpyridine, quinoxaline, quinoline, cinnoline, pteridine, carbazole, carboline, phenanthridine, acridine, phenanthrodine, isothiazole, phenazine, isoxazole, phenoxazine, phenothiazine, imidazolidine, imidazoline etc., and N-oxide and N-alkoxyl derivative of heteroaryl-containing compounds, e.g., pyridine-N-oxide derivatives.

The term "heteroalicyclic" refers to a saturated or partly unsaturated group of C3-C7 mono-cyclic ring or two or three fused-rings, in which 1-5 ring-carbon atoms are substituted by a heteroatom selected from N, S, P and/or O, preferably 1-3 heteroatoms, and in an embodiment with one or more fused rings, the functional group has no more than 16 carbon atoms. Examples of the heteroalicyclic are tetrahydrofuyl, morpholinyl, piperidyl, piperazinyl, dihydropyridinyl, etc.

The term "nucleotide" refers to a nucleoside in which a 5'-hydroxyl group binds to a is phosphoric acid.

The term "polynucleotides" refers to more than two nucleosides connected by a phosphoric acid in 5'-3' order, in which a terminal 5'-hydroxyl group binds to the phosphoric acid.

The term "enzymatically reactive moiety" refers to a functional group that can generate a hydroxyl group through an enzymatic reaction at physiological conditions, a typical example being a hydroxyl protecting group, e.g., nucleotide, polydinucleotide, acyl, acylamino.

The term "camptothecin pro-drug" and "CPT pro-drug" refers to a camptothecin derivative with a biologically degradable 20(S)-hydroxyl protecting group. The 20(S)-hydroxyl protecting group can be slowly cleaved by a specific enzyme at the physiological condition, releasing pharmaceutically active camptothecin.

The term "optionally substituted" means that the substitution on a group (or a functional group) is optional, so that a group, such as thymine, can be substituted or unsubstituted.

The present invention is based on the strategy that the 20(S)-hydroxyl is protected by a specific functional group which imparts a suitable level of stability to the E-ring lactone, and the resulting pro-drug can undergo cleavage through enzymolysis (bio-degradation) to release CPT components.

The present invention relates to a novel water-soluble 20(S)-O-nucleotide CPT derivative with the chemical structure of Formula I and its pharmaceutically acceptable salts,

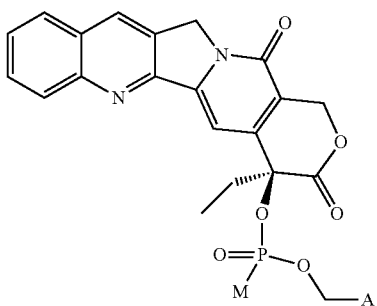

Formula I wherein M represents hydroxyl or thiol, A represents a nucleoside or its analog.

In one embodiment of the present invention, the 20(S)-O-nucleotide CPT derivative has the chemical structure of Formula II.

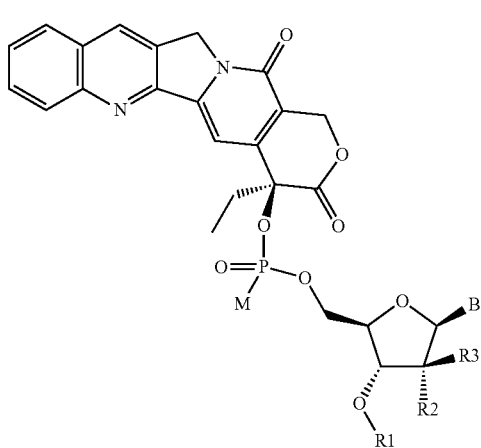

Formula II

Wherein M represents hydroxyl or thiol, preferably hydroxyl; R1 represents H; C1-C4 acyl, preferably acetyl; optionally substituted polynucleotide, preferably optionally substituted polydinucleotide; or an enzymatically reactive (particularly, cleavable) moiety, e.g. —RCOOR' and —NH-COR, wherein R and R' are C1-C4 alkyl or alkenyl, .e.g. C2 or C3 alkenyl;

R2 and R3 may be the same or different, independently representing hydrogen, halogen, hydroxyl, alkoxyl, or the hydroxyl group that is protected by an enzymatically reactive (particularly, cleavable) moiety (e.g. acetyl);

B is thymine, adenine, cytosine, guanine, uracil, 5-fluorouricil, 5-aza-cytosine, 2-fluoroadenine, 2-chloroadenine, hydrogen, optionally substituted thymine, optionally substituted adenine, optionally substituted cytosine, or an optionally substituted guanine, the optional substituents herein preferably are alkyl, aryl, or heteroaryl or heteroalicyclic group, wherein the heteroaryl or heteroalicyclic group preferably having from 1 to 3 mono-cyclic or fused-rings, and 1 to 3 N, O or S atoms in each ring; alternatively or in an alternative embodiment B is heteroaryl or heteroalicyclic group other than adenine, thymine, cytosine or guanine, having 1 to 3 mono-cyclic rings and 1 to 3 N, O or S atoms. In Formula I and Formula II, amino and hydroxyl of the A moiety may be protected by protecting groups known in the art. Preferred amino-protecting groups include acetyl, benzoyl, isobutyryl, tert-butyloxycarbonyl, formyl, benzyl, p-methoxybenzyloxycarbonyl, trityl, or the like. Preferred hydroxyl protecting groups include acetyl, trifluoroacetyl, pivaloyl, benzoyl, alkylcabonyl, alkyl, methyl, methoxymethyl, benzyloxymethyl, benzyl, trimethylsilyl, t-butyldimethylsilyl, or the like. Other suitable protecting groups as known to those skilled in the art are disclosed in Greene, T., Wuts, P. G. M., Protective Groups in Organic Synthesis, Wiley (1999), the disclosure of which is incorporated herein by reference. Preferred protecting groups for hydroxyl and amino include enzymatically reactive (particularly, cleavable) moieties is such as amide, ester, and the like.

In preferred embodiments of the present invention, the nucleoside moiety in Formula I and Formula II represents 5-fluoro-2'-deoxyuridine (floxuridine), thymidine, cytidine, guanosine, adenosine, 1',2'-deoxyribose, decitabine, azacitidine, gemcitabine, clofarabine, cladribine, pentostatin, wherein the 5'-oxygen of the nucleoside analogs are covalently linked to the phosphorus atoms. In Formula II, the nucleoside moiety preferably has R2, R3 and B in combinations or in sequences as listed in Table 1. Some of the nucleosides or nucleoside analogs listed herein, e.g. thymidine, cytidine, guanosine, adenosine, etc., are proven to cause no harm to human at the effective dose level of the drugs, and other nucleosides or nucleoside analogs, e.g. floxuridine, clofarabine, cladribine, pentostatin, etc., have been clinically used as anticancer drugs.

More preferably in the present invention, the R2, R3 and B are combined according to combinations or sequences listed in Table 1.

In a further preferred embodiment of the inventive composition with combinations or sequences of Table 1, R1 in Formula II is hydrogen or acetyl.

TABLE 1

| Number | Nucleoside name | M | R2 | R3 | B |
|---|---|---|---|---|---|
| 1 | thymidine | OH | H | H | ![thymine] |
| 2 | cytidine | OH | H | H | ![cytosine] |
| 3 | guanosine | OH | H | H | ![guanine] |
| 4 | adenosine | OH | H | H | ![adenine] |
| 5 | 1',2'-dideoxyribose | OH | H | H | H |

TABLE 1-continued

| Number | Nucleoside name | M | R2 | R3 | B |
|---|---|---|---|---|---|
| 6 | floxuridine | OH | H | H | (5-fluorouracil) |
| 7 | decitabine | OH | H | H | (5-azacytosine) |
| 8 | azacitidine | OH | OH | H | (5-azacytosine) |
| 9 | gemcitabine | OH | F | F | (cytosine) |
| 10 | clofarabine | OH | F | H | (2-chloroadenine) |
| 11 | cladribine | OH | H | H | (2-chloroadenine) |
| 12 | pentostatin | OH | H | H | (deoxycoformycin base) |
| 13 | fludarabine | OH | H | OH | (2-fluoroadenine) |

In the preferred embodiments described in Table 1, the hydrogen of hydroxy and/or amino of the moiety A in Formula I can be un-substituted or can be substituted with acyl or halogen, such as acetyl, chloride and fluoride. Therefore, the preferred compounds of the present invention of Formula II include the following chemicals:

Dix-905

$C_{29}H_{26}FN_4O_{11}P$
M.W. 656.5

Dix-906

$C_{30}H_{29}N_4O_{11}P$
M.W. 652.6

Dix-903

$C_{28}H_{27}N_6O_{11}P$
M.W. 654.5

Dix-904
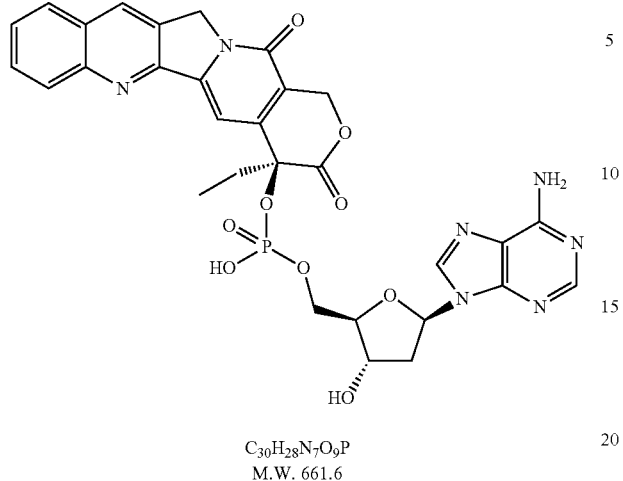
C₃₀H₂₈N₇O₉P
M.W. 661.6
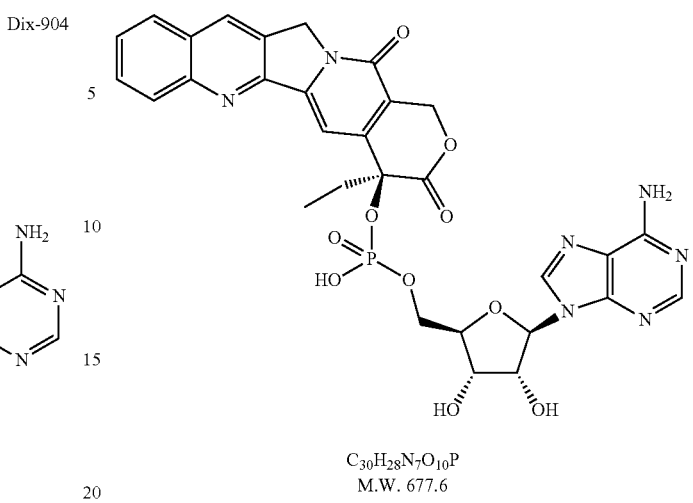
C₃₀H₂₈N₇O₁₀P
M.W. 677.6
Dix-902
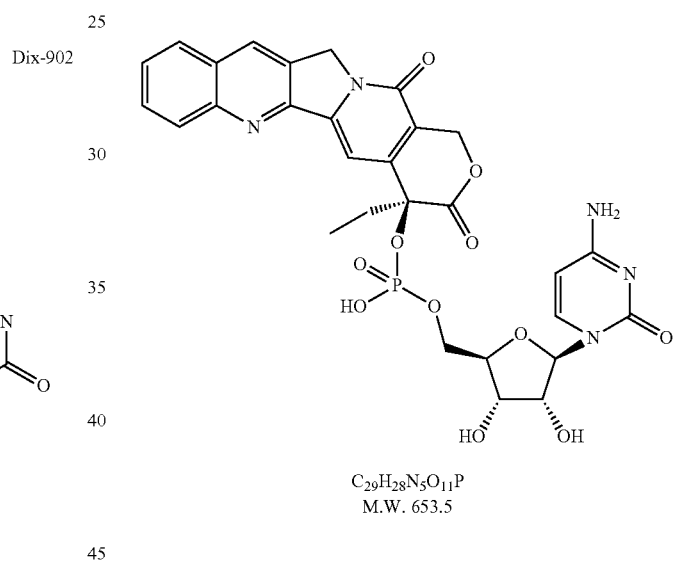
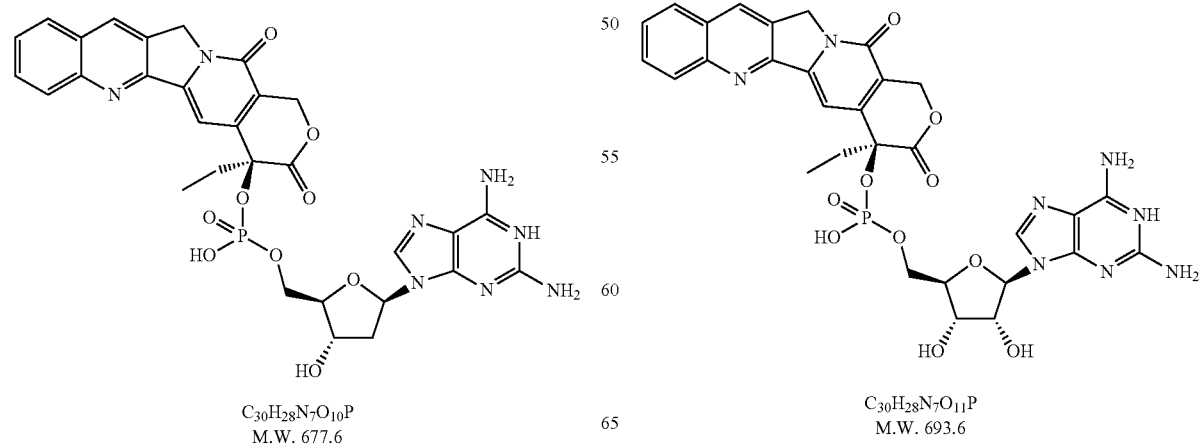
C₂₉H₂₈N₅O₁₀P
M.W. 637.5
C₂₉H₂₈N₅O₁₁P
M.W. 653.5
C₃₀H₂₈N₇O₁₀P
M.W. 677.6
C₃₀H₂₈N₇O₁₁P
M.W. 693.6

13
-continued
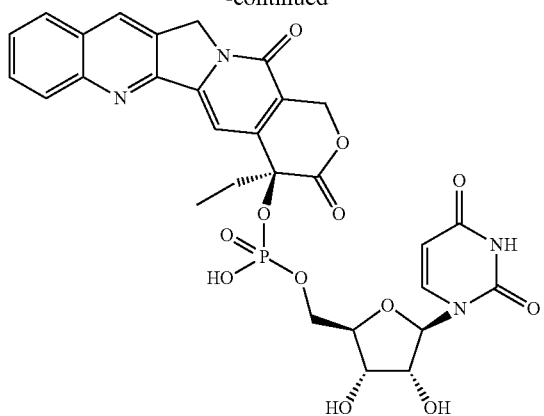
C29H27N4O12P
Mol. Wt.: 654.52
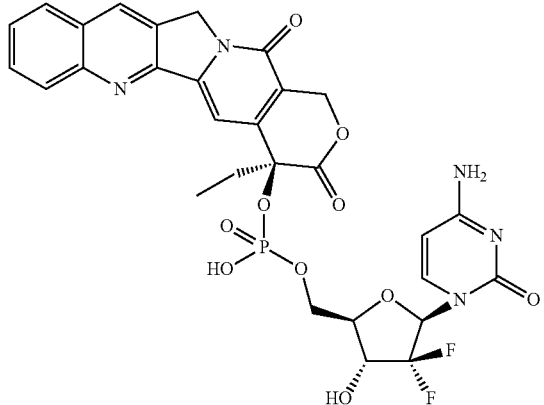
C29H26F2N5O10P
Mol. Wt.: 673.51
C28H27N6O10P
Mol. Wt.: 638.52
14
-continued
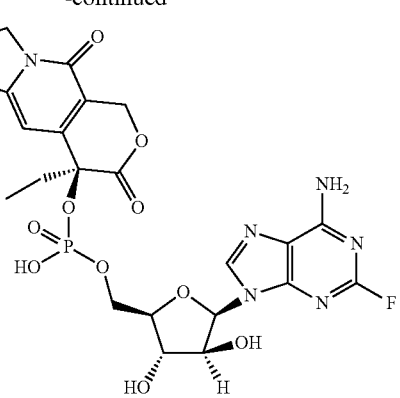
C30H27FN7O10P
M.W. 695.6
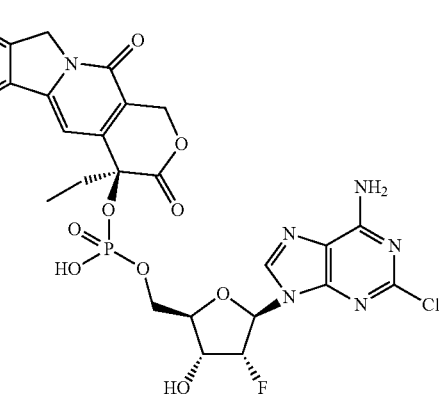
C30H26ClFN7O9P
M.W. 714
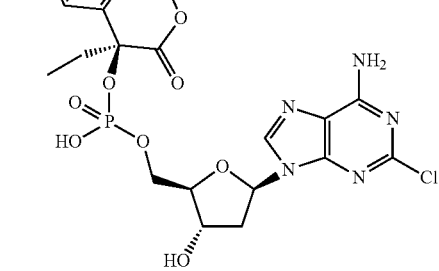
C30H27ClN7O9P
M.W. 696

15
-continued
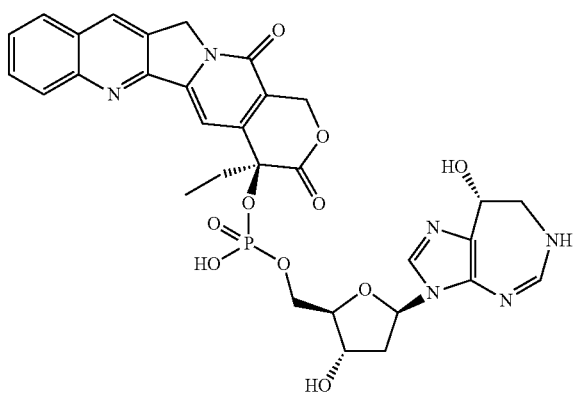
C31H31N6O10P
M.W. 678.6
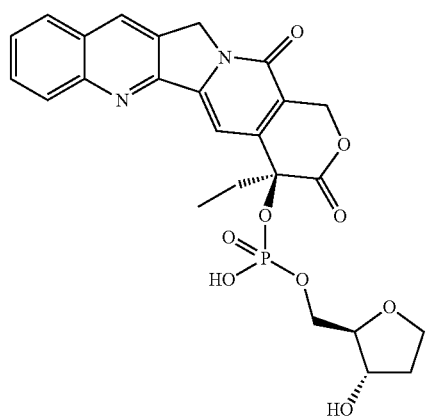
C25H25N2O9P
M.W. 528.4
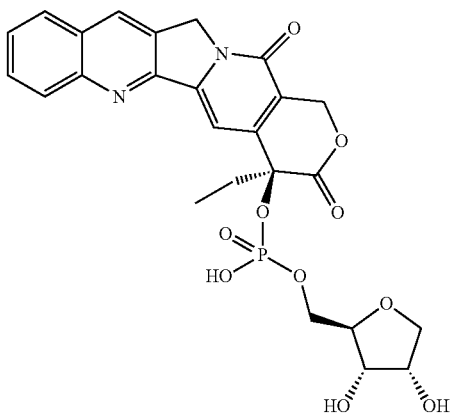
C25H25N2O10P
M.W. 544.4
16
-continued
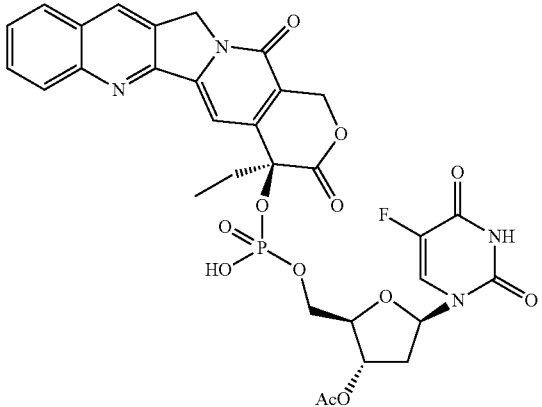
C31H28FN4O12P
Mol. Wt.: 698.55
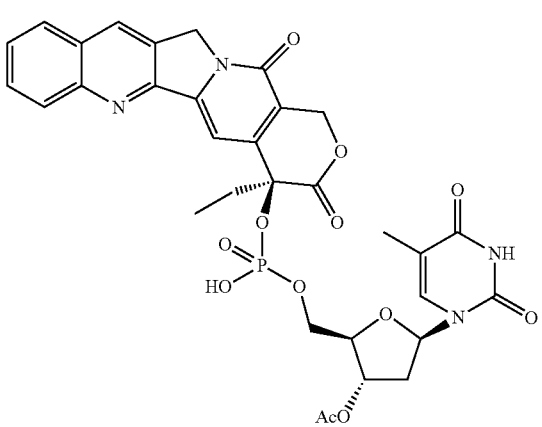 [SMILES: CC[C@@]1(OP(=O)(O)OC[C@H]2O[C@@H](n3cc(C)c(=O)[nH]c3=O)C[C@@H]2O)C(=O)OCc2c1cc1n(c2=O)Cc2cc3ccccc3nc2-1]
C32H31N4O12P
Mol. Wt.: 694.58
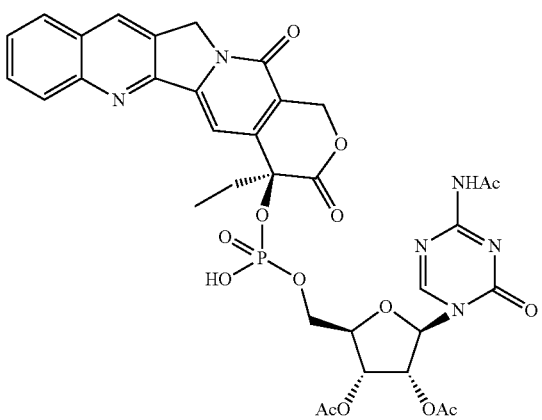
C34H33N6O14P
Mol. Wt.: 780.63

17
-continued
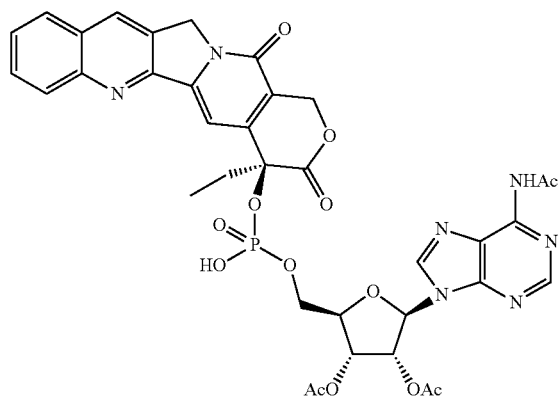 [SMILES: CC[C@@]1(OP(=O)(O)OC[C@H]2O[C@@H](n3cnc4c(N)ncnc43)C[C@@H]2O)C(=O)OCc2c1cc1n(c2=O)Cc2cc3ccccc3nc2-1]
C$_{36}$H$_{34}$N$_7$O$_{13}$P
Mol. Wt.: 803.67
18
-continued
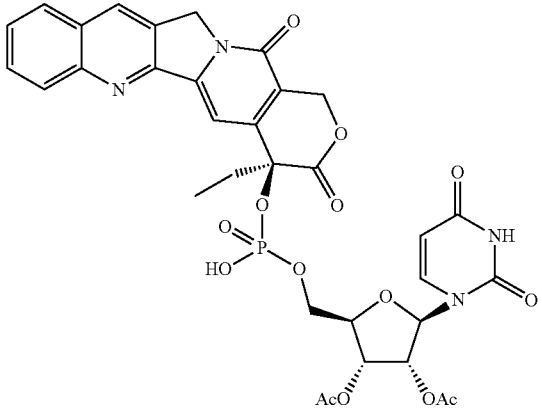
C$_{31}$H$_{29}$N$_4$O$_{13}$P
Mol. Wt.: 696.55
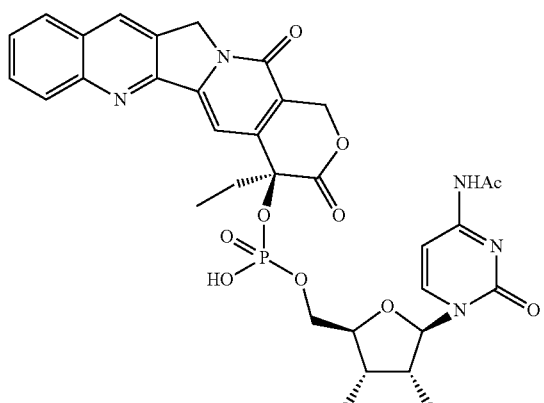
C$_{35}$H$_{34}$N$_5$O$_{14}$P
Mol. Wt.: 779.64
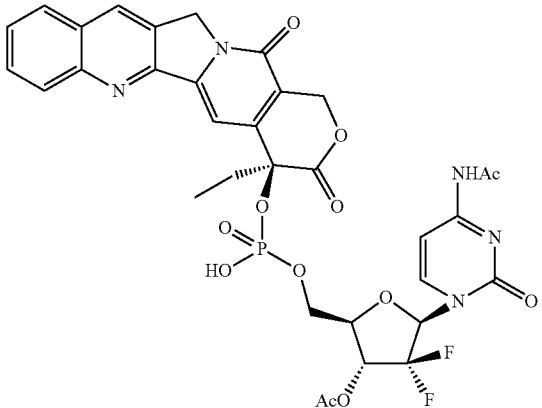
C$_{33}$H$_{30}$F$_2$N$_5$O$_{12}$P
Mol. Wt.: 757.59
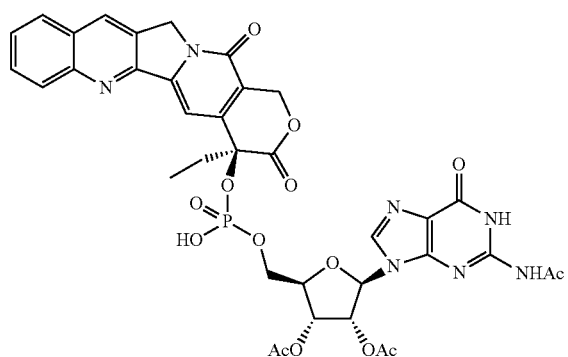
C$_{36}$H$_{34}$N$_7$O$_{14}$P
Mol. Wt.: 819.67
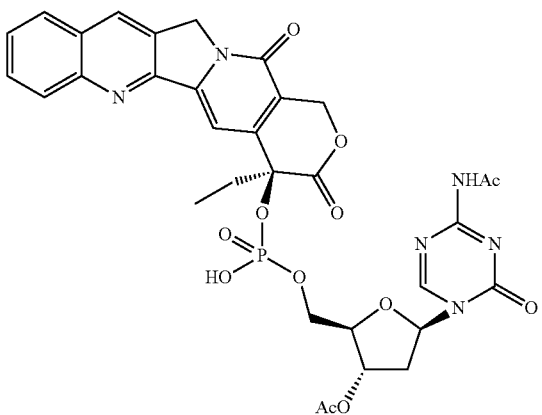 [SMILES: CC[C@@]1(OP(=O)(O)OC[C@H]2O[C@@H](n3ccc(N)nc3=O)C[C@@H]2O)C(=O)OCc2c1cc1n(c2=O)Cc2cc3ccccc3nc2-1]
C$_{32}$H$_{31}$N$_6$O$_{12}$P
Mol. Wt.: 722.6

-continued

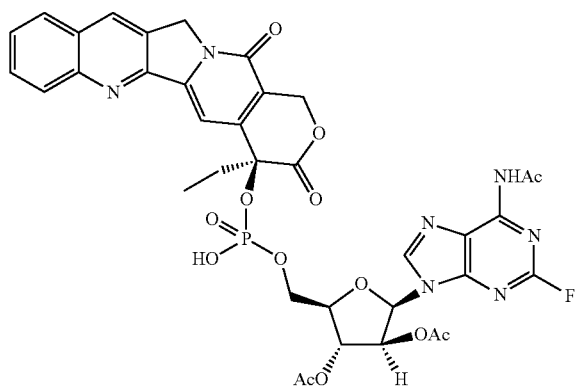

C$_{36}$H$_{33}$FN$_7$O$_{13}$P
Mol. Wt.: 821.66

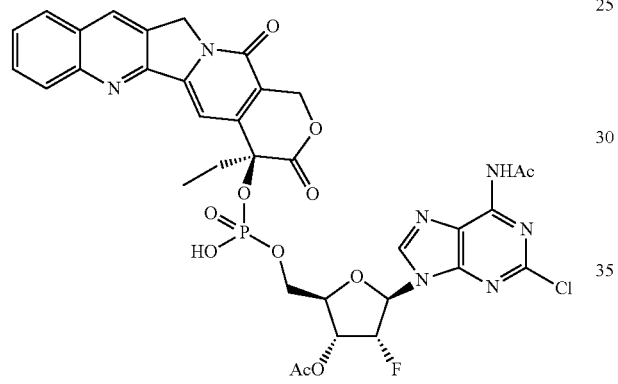

C$_{34}$H$_{30}$ClFN$_7$O$_{11}$P
Mol. Wt.: 798.07

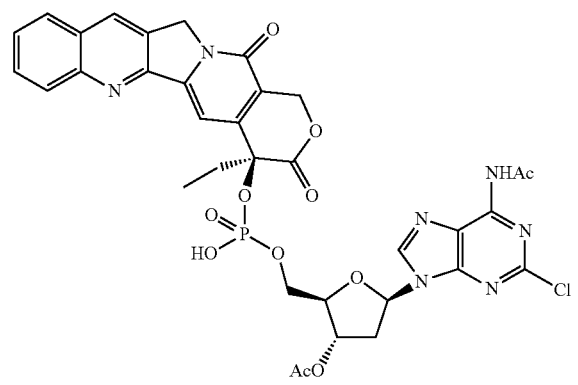

C$_{34}$H$_{31}$ClN$_7$O$_{11}$P
Mol. Wt.: 780.08

-continued

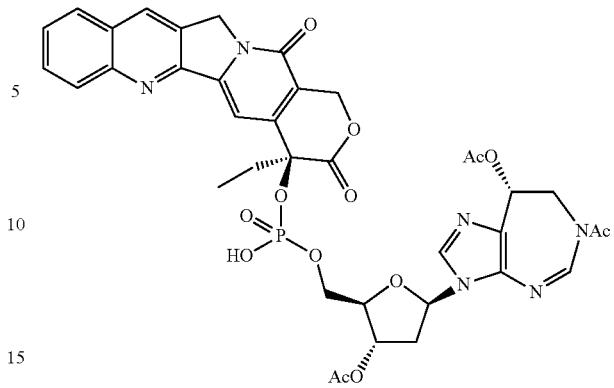

C$_{37}$H$_{37}$N$_6$O$_{13}$P
Mol. Wt.: 804.7

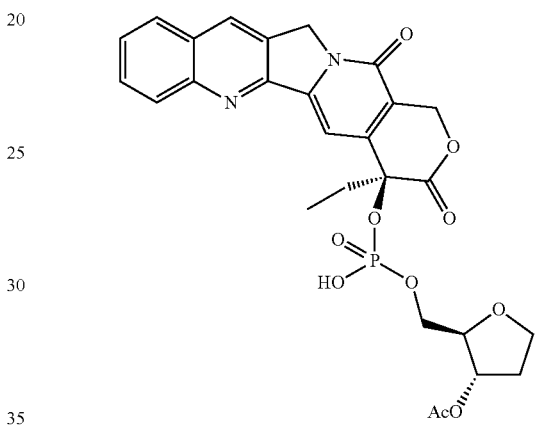

C$_{27}$H$_{27}$N$_2$O$_{10}$P
Mol. Wt.: 570.48

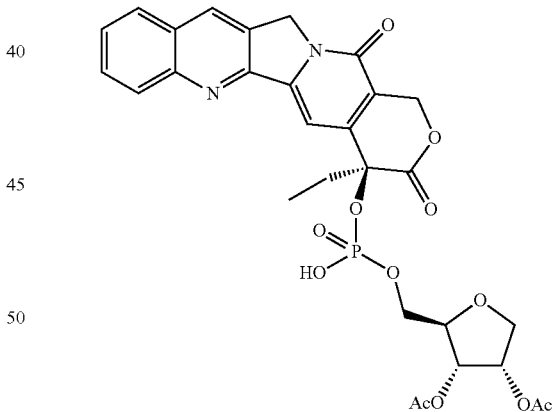

C$_{29}$H$_{29}$N$_2$O$_{12}$P
Mol. Wt.: 628.52

The above-described CPT derivatives of Formula I and Formula II can be used as the pro-drugs of CPT. Conversion of the pro-drugs of Formula I and Formula II to the corresponding CPT and 5'-phosphate nucleotides can be mediated by a group of enzymes known as phosphodiesterases in mammals. The compounds of Formula I and Formula II of the present invention rapidly distribute throughout the body within a short period of time after being administered into the blood stream, then converted through phosphodieserases to CPT and the 5'-phosphate nucleosides (when B is not hydrogen).

The above-described CPT derivatives of the present invention have good water solubility and CPT lactone stability, and can be metabolized to produce CPT at the physiological conditions. The derivatives of the present invention avoid precipitation of is CPT in the blood stream, resulting in lower toxicity and higher efficacy.

Preferably, when B is a nucleoside analog, the CPT derivative of the present invention can produce a second bioactive compound at the physiological conditions. Many nucleoside analogs are known to have anti-tumor activity and used clinically as anti-cancer agents, including but not limited to, 5-fluoro-2'-deoxyuridine (floxuridine), decitabine, azacitidine, gemcitabine, clofarabine, cladribine, pentostatin. All of these nucleosides require phosphorylation to be effective, and function primarily as antimetabolites and DNA replication inhibitors. Therefore, having one or more of the above nucleoside elements in the CPT derivative of the present invention may enhance therapeutic effects.

Preparation of the 20(S)-O-nucleotide camptothecin derivative of Formula II is carried out preferably as depicted in Scheme 1 by the phosphoramidite or phosphoramidite ester chemistry. Where M is a thiol, the synthesis is followed by a similar approach except for using Beaucage reagent in the final step.

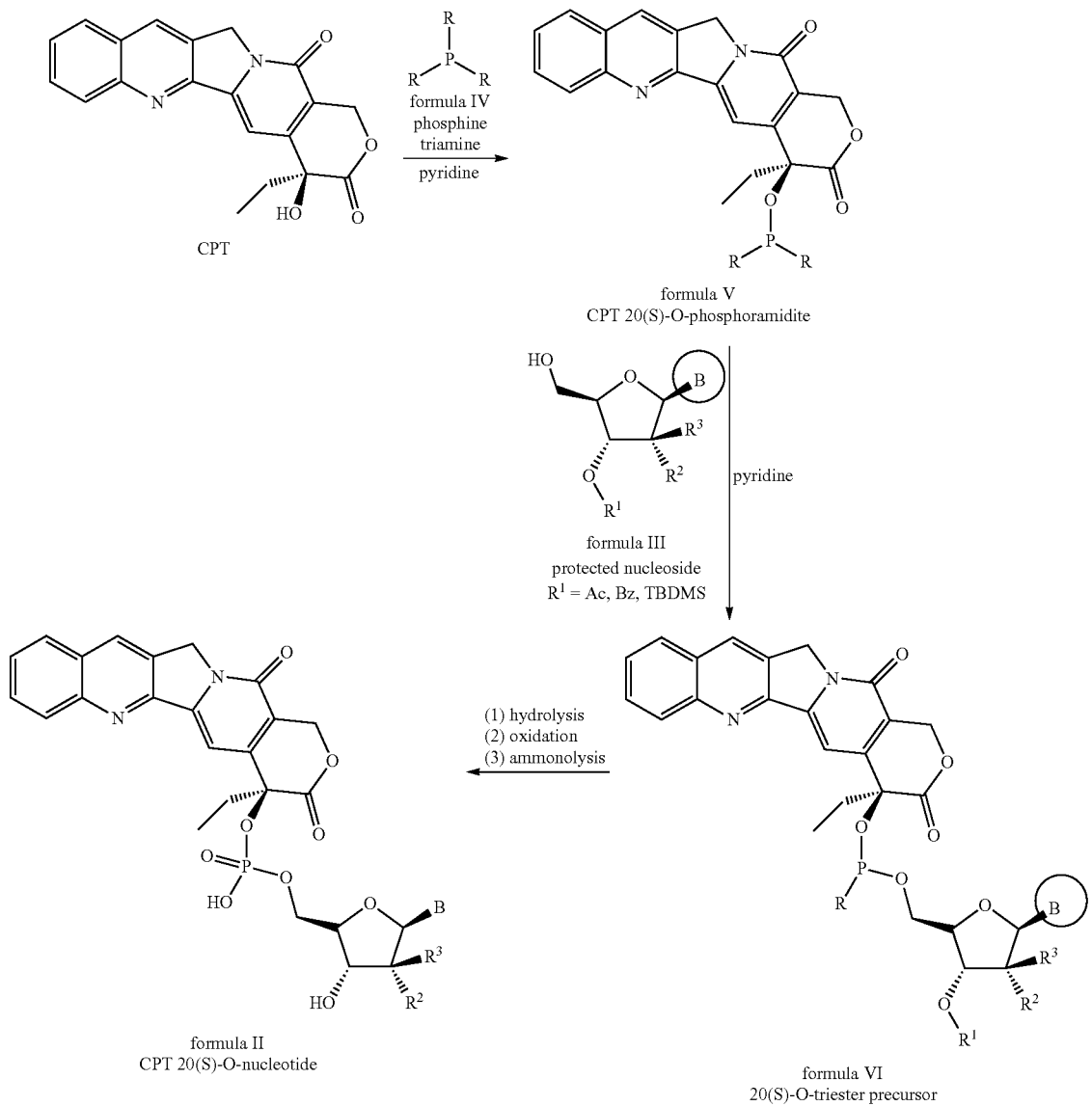

B = hydrogen or optionally substituted nucleobase, including thymidine, adenine, cytosine, guanine, uracil, 5-fluorouricil, 5-aza-cytosine, 2-fluoroadenine, 2-chloroadenine.

Ⓑ = protected B wherein the amino group is protected with suitable protecting group including acetyl or acyl group.

In Scheme 1, via the CPT 20(S)-O-phosphoramidite intermediate, the synthesis includes the following steps:

(1) reacting $PCl_3$ with an azole of RH, producing a phosphine triamine reagent of Formula IV:

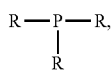

Formula IV wherein, R is

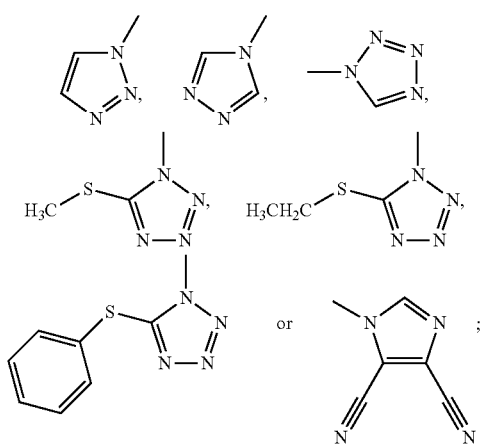

(2) reacting the phosphine triamine reagent of Formula IV with CPT, producing a CPT 20(S)-O-phosphoramidite mono-ester intermediate of Formula V:

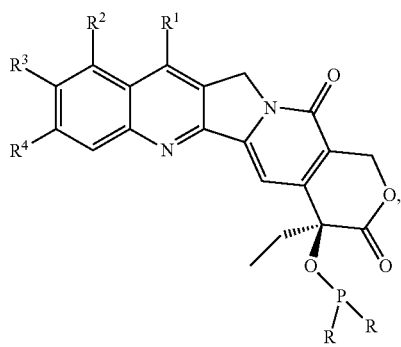

Formula V (3) reacting the CPT 20(S)-O-phosphoramidite mono-ester intermediate of Formula V with the suitably protected compound of Formula III, producing a 20(S)-O-phosphoramidite di-ester precursor of Formula VI;

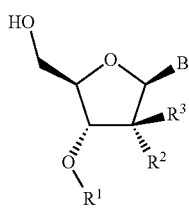

Formula III

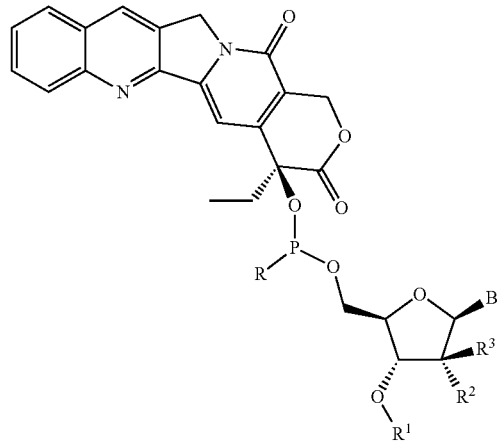

Formula VI wherein R1, R2, R3, and R4 are as previously defined, and where R1 is H, it is substituted with a suitable protecting group before reacting with the compound of Formula III during the synthetic process of Scheme 1, and where R2 or R3 is hydroxyl, said hydroxyl is protected with a protecting group before reacting with the compound of Formula III during the synthetic process of Scheme 1, and where B has amino, the amino is protected with a protecting group before reacting with the compound of Formula III during the synthetic process of Scheme 1;

(4) hydrolyzing the 20(S)-O-phosphoramidite di-ester precursor of Formula VI, followed by oxidation and ammonolysis to remove the protecting group, producing the CPT 20(S)-O-nucleotide CPT derivative of Formula II;

(5) converting the compound of Formula II into a corresponding salt by reacting the compound with a base, providing the corresponding salt. The bases that can be used in this step include, but are not limited to, NaOH, $Na_2CO_3$, $NaHCO_3$, KOH, $KHCO_3$, $K_2CO_3$, LiOH, $LiHCO_3$, $Li_2CO_3$, $NH_4HCO_3$, $Ca(OH)_2$, $CaCO_3$, $Ca(HCO_3)_2$, $Mg(HCO_3)_2$, $Zn(HCO_3)_2$, $Zn(OH)_2$, and $Fe(OH)_3$, and when a quaternary ammonium salt is desired, a corresponding quaternary ammonium base is used.

According to an embodiment of the present inventive method as illustrated in Scheme 1, anhydrous triazole (3 equivalents) and newly distilled pyridine are added into a dry reaction vessel under protection of inert gas, followed by addition of phosphorus trichloride (1.5 equivalents) while cooling in an ice-bath. Then the ice-bath is removed. After stirring for 0.2-5 hours at room temperature, anhydrous CPT (1.5 equivalents) dissolved in newly distilled pyridine is added. This mixture is stirred continuously for 1-12 hours at room temperature until CPT is completely consumed or converted. Then, suitably protected 5'-OH nucleoside (1-3 equivalents) which is pre-dissolved in newly distilled pyridine is added. After stirring for 0.2-5 hours, 20(S)-O-phosphoramidite di-ester of Formula VI is generated, which subsequently undergoes oxidation with iodine (2-10 equivalents) in aqueous THF or peroxide (e.g. hydrogen peroxide, t-butyl hydroperoxide) for 10 minutes to produce a CPT 20(S)-O-nucleotide derivative with suitable protecting group(s). The protecting group(s) is of the nucleoside moiety for the CPT 20(S)-O-nucleotide can be removed by treating with ammonia or methylamine/ethanol (>10 equivalents) at elevated temperature (30-60° C.). After evaporating the solvent, the water-soluble crude or raw product is purified by extraction and is further purified through the C18 chromatography and/or desalting, followed by freeze-drying to yield a solid end product with a slightly yellow color.

Any nucleoside analog that has 5'-hydroxyl group may be used as starting materials of the nucleotide in the above-mentioned scheme. Preferred nucleosides for use in the present invention have the structure of Formula III, including, but are not limited to, thymidine, cytidine, guanosine, adenosine, 1',2'-deoxyribose, 5-fluoro-2'-deoxyuriudine (floxuridine), decitabine, azacitidine, gemcitabine, clofarabine, cladribine, and pentostatin. Except for 5'-hydroxyl, amino or the other hydroxyl groups of the above nucleoside of Formula III are protected with suitable protecting groups before being used as the starting materials.

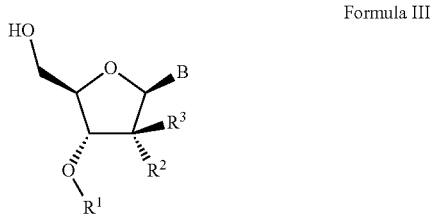

Formula III

In Formula III, it is understood that amino and hydroxyl can be protected by a protecting group known in the art. Preferred protecting groups for amino groups include acetyl, benzoyl, isobutyryl, tert-butyloxycarbonyl, formyl, benzyl, p-methoxybenzyloxycarbonyl, trityl, or the like. Preferred protecting groups for the hydroxyl groups include acetyl, trifluoroacetyl, pivaloyl, benzoylcarbonyl, alkyl, methyl, methoxymethyl, benzyloxymethyl, benzyl, trimethylsilyl, t-butyldimethylsilyl, or the like. Other suitable protecting groups as known to those skilled in the art are disclosed in Greene, T., Wuts, P. G. M., Protective Groups in Organic Synthesis, Wiley (1999), the disclosure of which is incorporated herein by reference. Preferred protecting groups for hydroxyl and amino groups include enzymatically reactive (particularly, cleavable) moieties such as amide, ester, and the like.

The compounds of Formula I of the present invention are effective in treating cancers, including, but are not limited to, malignant tumors and other forms of cancer. As used herein, the term "malignant tumor" is intended to encompass all forms of human carcinomas, sarcomas, and melanomas which occurs in the poorly differentiated, moderately differentiated, and well differentiated forms. In administering the compounds of the present invention to patients in need of such treatment, an is effective amount of the compound or formulation containing one or more compounds of the present invention is administered to the patient. As used herein, an "effective amount" of the compound of the present invention is intended to mean the amount of the compound that will inhibit the growth of, or retard cancer, or kill cancer or malignant cells, and/or cause the regression and/or palliation of cancer such as malignant tumors, i.e., reduce the volume or size of such tumors or eliminate the tumor entirely.

The compounds of the present invention and the formulations of the present invention can be used in the treatment of a variety of tumors and/or cancers including, but are not limited to, cancers of the human lung, breast, colon, prostate, melanoma, pancreas, stomach, liver, brain, kidney, uterus, cervix, ovaries, urinary track, gastrointestinal, and other solid tumors that grow in anatomical sites other than the blood stream, as well as blood borne tumors such as leukemia. Other solid tumors suitable for the present invention include, but are not limited to, colon and rectal tumors. The compounds of the present invention are also useful as inhibitors of the enzyme topoisomerase I. Some of the camptothecin analogs of the present invention can be converted into pharmaceutically acceptable salts by reacting with inorganic acids such as, but are not limited to, hydrochloride, hydrobromide, sulfate, phosphate, and nitrate. The camptothecin analogs can also be converted into salts with organic acids such as, but are not limited to, acetate, tartrate, fumarate, succinate, citrate, methanesulfonate, p-toluenesulfonate, and stearate. Other acids can be used as intermediates during the preparation of the compounds of the present invention and their pharmaceutically acceptable salts.

The present invention also provides a method of treating a patient, which comprises administering a pharmaceutically effective amount of a compound of the present invention. The compound may, for example, be administered to a patient with cancer and/or leukemia. The compounds of the present invention may also act as anti-viral (for example, anti-HIV) agents and anti-parasitic agents. The pharmaceutically effective amount or dosage is preferably between 0.1 to 100 mg of a compound of Formula I per kg of body weight. More preferably, the pharmaceutically effective amount or dosage is preferably between 0.1 to 40 mg of a compound of Formula I per kg of body weight. In general, a pharmaceutically effective amount or dosage contains the amount of a compound that effectively demonstrates certain anti-leukemic and/or anti-tumor properties. Pharmaceutical compositions containing, as an active ingredient, one of the compounds of the present invention, including a pharmaceutically acceptable salt thereof, in association with a pharmaceutically acceptable carrier or diluent, are also within the scope of the present invention.

The compounds of the present invention may be administered in a dose that is effective for inhibiting enzyme topoisomerase I, generally from about 0.1-100 mg/kg of body weight per week, preferably about 0.1-40 mg/kg per week.

The compounds of the present invention may be administered as a pharmaceutical formulation, which includes the compounds and a pharmaceutically acceptable carrier or diluent. The pharmaceutical formulation can also include other active ingredients which do not impair the desired action and/or supplement the desired action. The compounds (active ingredients) according to the present invention can be administered by any suitable route, for example, orally, nasally, parenterally, intravenously, intradermally, subcutaneously, or topically, in liquid or solid forms.

For the purposes of parenteral therapeutic administration, the active ingredient may be incorporated into a solution or suspension. The solution or suspension may also include the following components: a sterile diluent, such as water, for injection; a suspension of liposomal particles, which contain a stable, active drug ingredient within the core of the liposomal particle in a pH controlled and protected environment, or contains an active drug ingredient associated to the outside of the liposomal particle or any of the bilayers of the liposomal particle; solvents, such as saline solution, fixed oils, polyethylene glycols, glycerine, propylene glycol or other synthetic solvents; antibacterial agents, such as benzyl alcohol or methyl parabens; antioxidants, such as ascorbic acid or sodium bisulfite; chelating agents, such as ethylenediaminetetraacetic acid; buffers, such as acetates, citrates or phosphates, and tonicity-adjusting agent, such as sodium chloride or dextrose. The parenteral formulation can be enclosed in ampoules, disposable syringes or multiple dose vials, all of which can be made of glass or plastic.

Another mode of administration of the compounds of this invention is oral. Oral compositions will generally include an inert diluent or an edible carrier. They may be enclosed in gelatin capsules or compressed into tablets. For the purposes of oral therapeutic administration, the aforesaid compounds may be formulated with suitable excipients into tablets, troches, capsules, elixirs, suspensions, syrups, wafers, chewing gums, or the like.

The tablets, pills, capsules and the like may contain the following ingredients: a binder, such as microcrystalline cellulose, gum tragacanth, or gelatin; an excipient, such as starch or lactose; a disintegrating agent, such as alginic acid, Primogel, corn starch or the like; a lubricant, such as magnesium stearate or Sterotes; a glidant, such a colloidal silicon dioxide; and a sweetening agent, such as sucrose or saccharin or flavoring agent such as peppermint, hmethyl salicylate, or orange flavoring may be is added. When the dosage unit is in the form of a capsule, it may contain, in addition to the above ingredients, a liquid carrier such as a fatty oil. Other dosage units may contain other ingredients that modify the physical form of the dosage unit, for example, coatings. Some preferred tablets or pills may be coated with sugar, shellac, or other enteric coating agents. A syrup formulation may contain, in addition to the active compounds, sucrose as a sweetening agent and certain preservatives, dyes and coloring and flavors. Ingredients used in these various formulations should be acceptable or suitable for use in human and veterinary medicines, and non-toxic in the amount used.

The term "20(S)-O-nucleotide camptothecin derivative" in the above description refers to the compound of Formula I.

The foregoing description of the specific embodiments fully reveals the general nature of the invention that others can, by applying current knowledge, readily modify and/or adapt for various applications of such specific embodiments without departing from the generic concept, and therefore such adaptations and modifications are understood or intended to be within the meaning and range of equivalents of the disclosed embodiments. It is to be understood that the terms used herein are merely descriptive, rather than limiting. The following examples are provided to further illustrate various embodiments of the invention and are not intended to limit the scope of the invention in any way.

EXAMPLE 1

Synthesis and Anticancer Evaluation of Dix-905

Compounds of Formula I of the invention include Compound Dix-905 of following chemical structure:

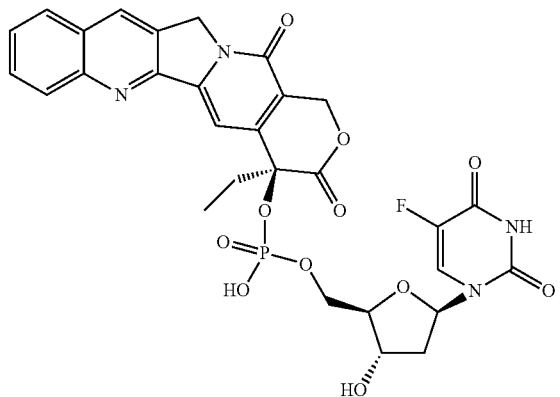

Dix-905

(a) Synthesis of Dix-905

Into a dry 100 mL round-bottom flask, added (in an ice bath) 317.5 mg anhydrous triazole (4.59 mmol), 20 ml newly distilled pyridine under the protection of Ar, and 0.2 ml phosphorus trichloride (2.29 mmol). After removing the ice-bath and then stirring at room temperature for 0.5 h, 500 mg anhydrous CPT in 20 mL newly distilled pyridine (1.43 mmol CPT) was added, and then stirred continuously at room temperature for 2 h. After CPT was completely consumed or converted, 3' Bz-5-FdU 1.24 g (3.60 mmol) in 20 mL newly distilled pyridine was added, and the mixture was stirred continuously for 0.5 h. After the material produced in the previous step was completely consumed, argon protection was removed and 5 mL 0.4 M $I_2$/THF solution added. The reaction was completed in about 1 min, with the solution turning purplish red. The solvent was removed through reduced pressure evaporation to give a yellow solid product, which was then dissolved in 5 mL of conc. ammonia to produce a brownish yellow solution. The solution was stirred at 60° C. for 3 h, turning into a bright yellow color, after which most of the solvent was removed by reduced pressure evaporation followed by passing through a reversed-phase column. The target eluent was collected, and most of the solvent was removed by reduced pressure evaporation followed by adjusting pH to 1 with diluted HCl solution and extracting three times with 15 mL dichloromethane. The organic phases from the extractions were collected and combined together. The combined organic phase underwent extraction with water, and the aqueous phase from the extraction was collected and condensed. The condensed aqueous phase passed through a reversed-phase column, producing 420 mg yellowish target solid product. (0.64 mmole), TLC and NMR results indicated that the product contained CPT 20(S)-nucleotide with higher than 90% of purity. ES-MS (negative detection mode): $C_{29}H_{25}FN_4O_{11}P$(655), found 655. 1H NMR (400 MHz, D2O): δ 9.195(s, 1H), 8.567(s, 1H), 8.377-8.308(d, 1H), 8.207(s, 1H), 8.107-8.094(d, 1H), 7.954-7.887(t, 1H), 7.690-7.584(t, 1H), 7.524(s, 1H), 5.742-5.691 (m, 1H), 5.521-5.418 (m, 2H), 4.665-4.618(d, 1H), 4.493-4.445(d, 1H), 4.370(s, 1H), 3.959-3.915(m, 2H), 3.800 (s, 1H), 2.386-2.289(m, 2H), 2.221-2.014(m, 2H), 1.064-1.027(t, 3H), 13C: δ 172.228, 159.579, 158.645, 151.554, 150.864, 148.157, 147.211, 145.426, 140.157, 131.415, 129.875, 128.754, 128.542, 128.225, 127.660, 126.547, 120.519, 110.875, 105.512, 99.588, 85.645, 85.245, 77.514, 71.655, 67.251, 50.255, 39.224, 11.245, 7.241. 31P: δ −2.324.

(b) Anticancer Evaluation

To determine the ability of Compound Dix-905 (also referred as Compound 905) to kill cancer cells, we performed a cell viability assay via CellTiter-Glo kit (Promega) using various cell lines. The kit measures the ATP levels via an enzymatic Luciferase assay. Viable cells, having normal metabolic rates and producing normal levels of ATP, will is have a high turnover of Luciferase substrates, which requires ATP for the enzymatic reaction and emits luminescent signals. By contrast, dying cells will have lower outcome of luminescent signals since their metabolic functions are diminished. The emitted luminescent signals will then be captured by a luminometer.

To perform the viability assay, small cell lung cancer cells (ATCC catalog No. H146), breast cancer cells (ATCC catalog No. MDAMB231) or colon cancer cells (ATCC catalog No. HCT116) were seeded in 96 wells and treated via Compound Dix-905 and other anti-cancer drugs for a time period of 24, 48, 72 hours. At each respective time point, cells were mixed with Cell Titer Glow reagents for 1 h and evaluated for luminescent signals.

For caspase activation, similar assays could be performed using the Caspase-Glo 3/7kit from Promega after cells were treated with respective agents for various time points. The mechanism of Caspase 3/7 Glow assay is by using Caspase 3/7 substrate fused with Luciferase substrate, which could be cleaved by activated Caspase 3/7. The released Luciferase substrate then undergoes an enzymatic reaction and emits luminescent signals. In contrast to the viability assay, the limiting step for this assay is caspase activation. Dying cells bearing the activated Casapses will have a high readout of luminescent signals in a luminometer.

(c) The anticancer activities of Dix-905 are summarized in FIGS. 1-8.

FIG. 1. Dix-905 triggered cell killing response better than that of CPT in H1693 cells.

Figure 2:
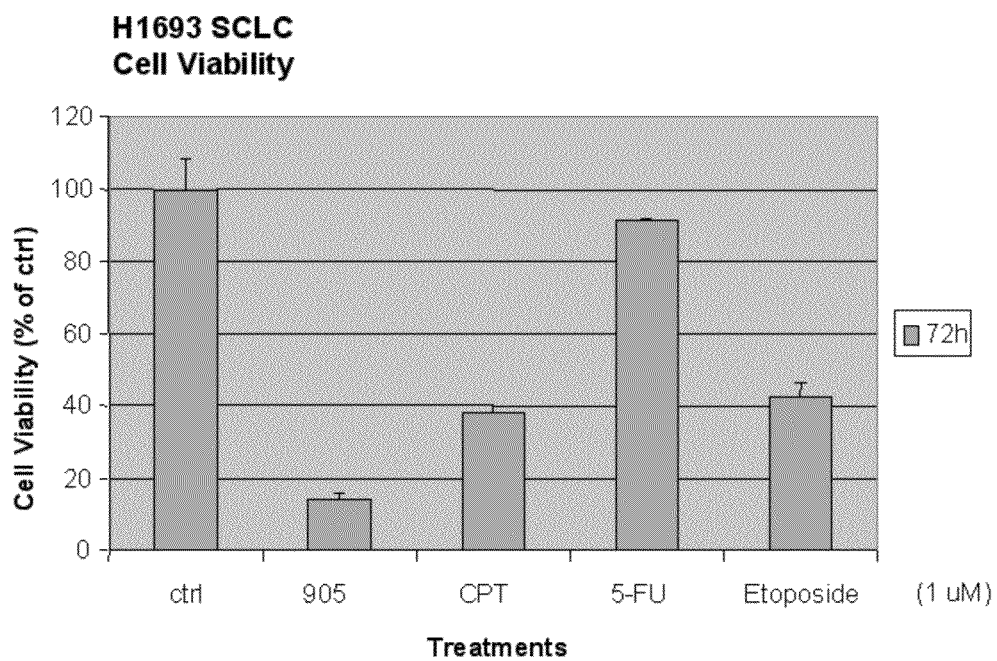
FIG. 2. Dix-905 treatments resulted in more effective cell killing in H1693 than that of CPT, floxuridine, and etoposide, due to synergistic effects.

FIG. 2. Dix-905 treatments resulted in more effective cell killing in H1693 than that of CPT, floxuridine, and etoposide, due to synergistic effects.

Figure 3:
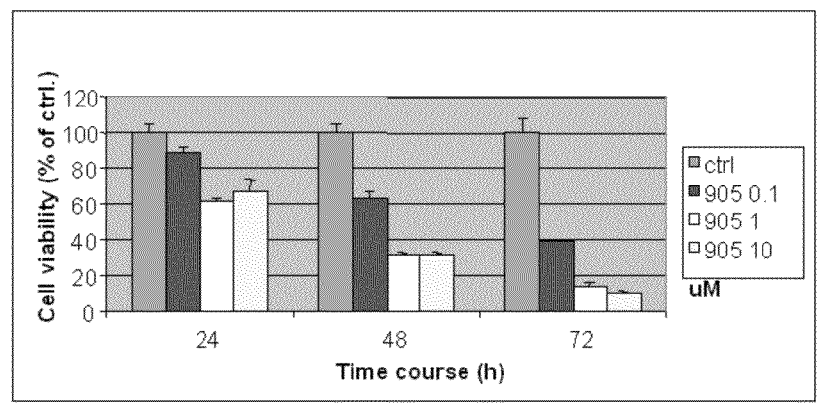
FIG. 3. Dix-905 triggered time- and dose-dependent cell death in H1693 via Caspase activation (apoptotic pathway).
Figure 3:
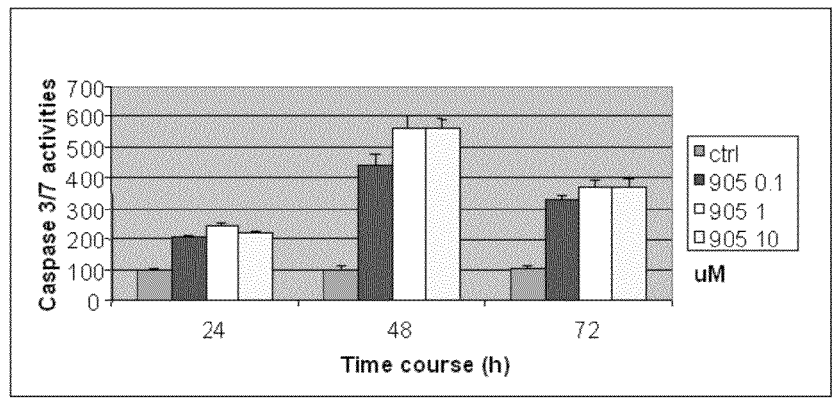

FIG. 3. Dix-905 elicited time- and dose-dependent cell death in H1693 via Caspase activation (apoptotic pathway).

Figure 4:
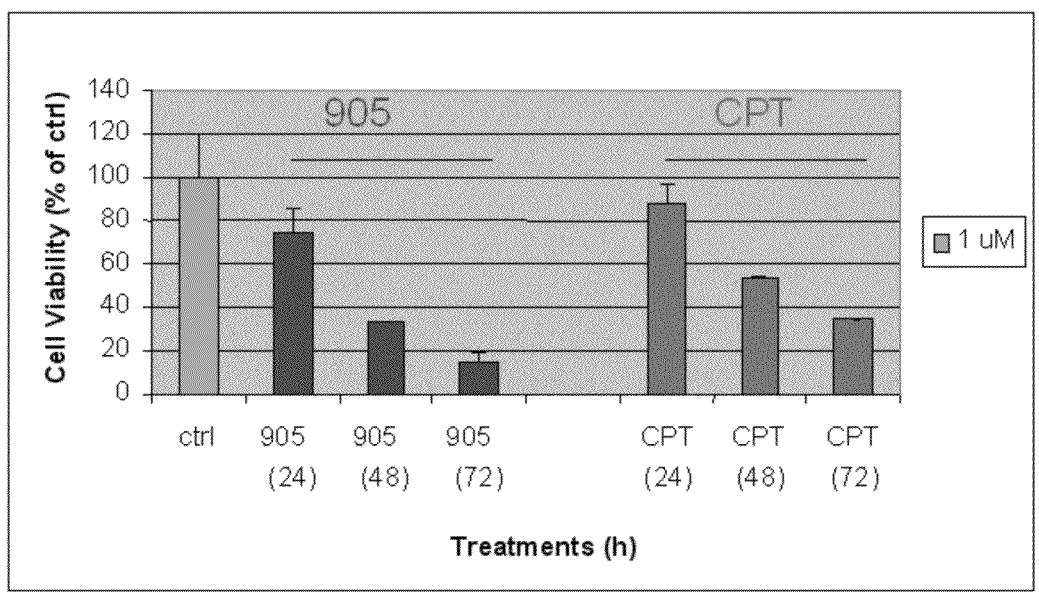
FIG. 4. Dix-905 triggered cell killing response in H146 better than that of CPT.

FIG. 4. Dix-905 elicited cell killing response in H146 better than that of CPT.

Figure 5:
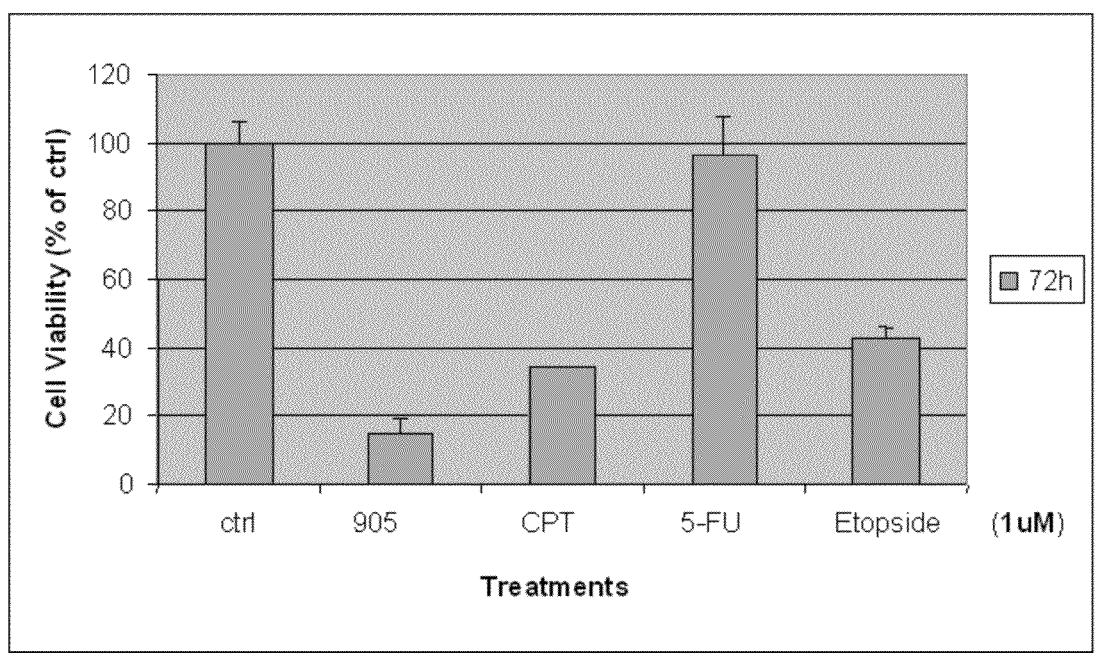
FIG. 5. Dix-905 triggered more effective cell killing in H146 than that of CPT, floxuridine and etoposide.

FIG. 5. Dix-905 triggered more effective cell killing in H146 than that of CPT, floxuridine, and etoposide.

Figure 6:
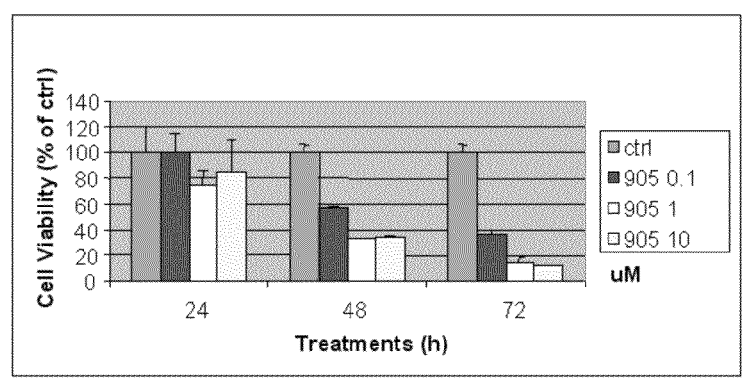
FIG. 6. Dix-905 triggered time- and dose-dependent cell death in H146 via Caspase activation (apoptotic pathway).
Figure 6:
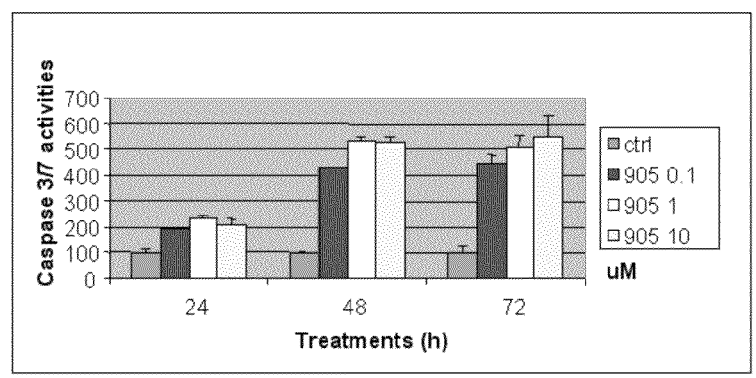

FIG. 6. Dix-905 elicited time- and dose-dependent cell death in H146 via Caspase activation (apoptotic pathway).

Figure 7:
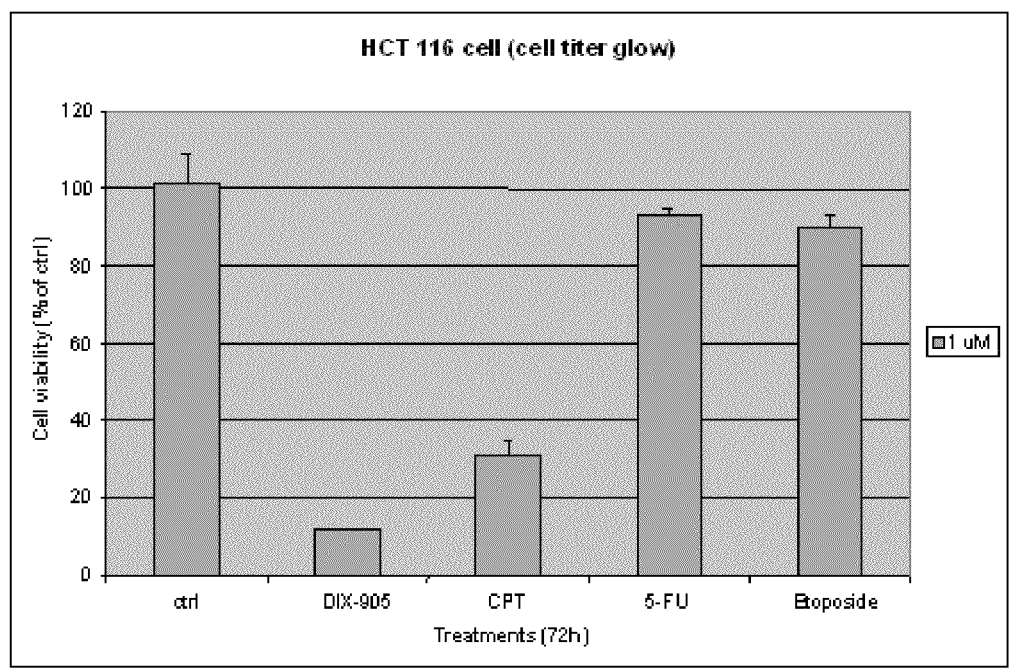
FIG. 7. DIX-905 was more effective in triggering cell death than that of CPT, 5-FU is and Etoposide in HCT116 colon cells.
Figure 8:
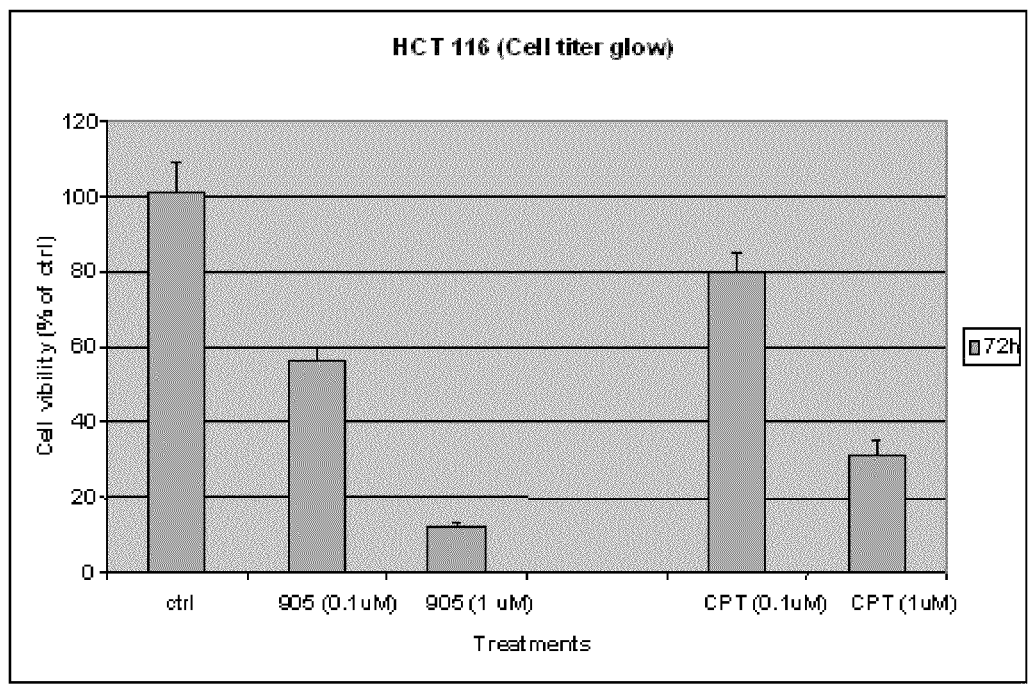
FIG. 8. Dose-dependent cell death by DIX-905 and CPT in HCT116 cells.

FIG. 7. DIX-905 was more effective in cell killing than that of CPT, 5-FU and Etoposide in HCT116 colon cells FIG. 8. Dose-dependent cell death by Dix-905 and CPT in HCT 116 cells.

EXAMPLE 2

By using the procedure of Example 1, other several representative compounds of Formula I were obtained as listed in Table 2. They were yellow solid products, stable at room temperature, not easily decomposed, with a solubility >10 mg/mL.

TABLE 2

| Material Abbreviation | Chemical Structure | Analytical Data |
|---|---|---|
| Dix-906 | 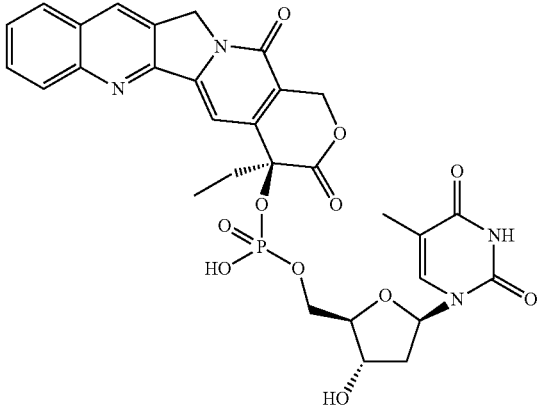 | 1H NMR (400 MHz, D2O): 8.377 (s, 1H), 7.921-7.901 (d, 1H), 7.788-7.767 (d, 1H), 7.708-7.672 (t, 1H), 7.605-7.558 (t, 1H), 7.492 (s, 1H), 7.194 (s, 1H), 5.639-5.606 (m, 1H), 5.592-5.487 (m, 2H), 4.937-4.889 (d, 1H), 4.800-4.748 (d, 1H), 4.394-4.380 (m, 1H), 4.015-3.816 (m, 2H), 3.809 (s, 1H), 2.414-2.281 (m, 2H), 2.241-2.182 (m, 1H), 2.033-1.965 (m, 1H), 1.493 (s, 3H), 1.031-0.994 (t, 3H), 13C: δ 172.156, 165.388, 157.755, 150.220, 150.224, 147.049, 146.095, 144.218, 136.237, 131.399, 129.564, 128.540, 128.380, 128.314, 127.741, 126.736, 120.472, 110.450, 104.779, 100.470, 85.788, 85.396, 77.112, 70.395, 67.129, 50.196, 39.423, 11.176, 7.153; 31P: δ –1.914; [M – 1] 651. |
| Dix-904 | 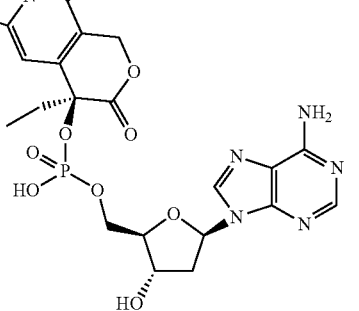 | 1H NMR (400 MHz, D2O): δ 9.234 (s, 1H), 9.008 (s, 1H), 8.474 (s, 1H), 8.124-8.100 (d, 1H), 7.912-7.894 (d, 1H), 7.801-7.790 (t, 1H), 7.711-7.695 (t, 1H), 7.558 (s, 1H), 7.432 (s, 1H), 5.551-5.520 (m, 1H), 5.510-5.461 (m, 2H), 4.910-4.872 (d, 1H), 4.724-4.686 (d, 1H), 4.457-4.441 (m, 1H), 4.116-3.918 (m, 2H), 3.8579 (s, 1H), 2.313-2.204 (m, 2H), 2.118-2.087 (m, 1H), 2.001-1.917 (m, 1H), 1.052-1.014 (t, 3H), 13C: δ 173.241, 166.412, 157.543, 151.547, 150.874, 147.541, 146.241, 144.478, 136.247, 131.574, 129.417, 128.547, 128.247, 128.047, 127.117, 126.117, 120.148, 118.954, 110487, 104.748, 100.544, 85.389, 85.547, 77.018, 70.017, 67.129, 50.117, 39.457, 11.478, 7.247; 31P: δ –2.145; [M – 1] 660. |

TABLE 2-continued

| Material Abbreviation | Chemical Structure | Analytical Data |
|---|---|---|
| Dix-902 | (structure shown) | 1H NMR (400 MHz, D2O): δ 8.726 (s, 1H), 8.628 (s, 1H), 8.075-8.055 (m, 2H), 7.895-7.855 (t, 1H), 7.829-7.793 (t, 1H), 7.661-7.625 (t, 1H), 7.406 (s, 1H), 5.912-5.897 (m, 1H), 5.737-5.721 (m, 1H), 5.379-5.334 (m, 1H), 5.260-5.212 (d, 1H), 5.127-5.079 (d, 1H), 4.845 (s, 1H), 3.724-3.702 (m, 1H), 3.627-3.488 (m, 2H), 2.470-2.064 (m, 4H), 0.808-0.772 (t, 3H), 13C: δ 172.203, 165.421, 157.245, 155.440, 150.241, 147.214, 146.158, 144.024, 136.154, 131.451, 129.411, 128.541, 128.452, 128.121, 127.854, 126.551, 120.474, 110.322, 104.887, 100.514, 85.854, 85.221, 77.214, 70.512, 67.414, 50.225, 39.441, 7.153; 31P: δ −2.421; [M − 1] 636. |

Examples 2-1, 2-2 and 2-3

Anticancer Evaluation of Dix-902, Dix-904 and Dix-906

By using the procedure of Example 1, the anticancer activities of Dix-902, Dix-904 and Dix-906 were measured, and the test results were summarized in Tables 3, 4 and 5 respectively.

Table 3 shows that compounds Dix-902, Dix-904 and Dix-906 triggered dose-dependent cell death in H146 (small cell lung cancer) cells. In the "CPT" group, the H146 (small cell lung cancer) cells were treated with CPT (dissolved in DMSO) in 4 concentrations (0, 0.1, 1.0, 10 μM, respectively) for 48 hours; In the Dix-902, Dix-904 and Dix-906 groups, H146 (small cell lung cancer) cells were treated respectively with the corresponding compounds (dissolved in a saline solution) in 4 concentrations (0, 0.1, 1.0, 10 μM, respectively) for 48 hours.

TABLE 3

H146 cell viability after 48 hours of treatment with CPT, Dix-902, Dix-904 and Dix-906.

| Conc. | Cell viability after treatment with CPT | Cell viability after treatment with Dix-902 | Cell viability after treatment with Dix-904 | Cell viability after treatment with Dix-906 |
|---|---|---|---|---|
| 0 μM | 100% | 100% | 100% | 100% |
| 0.1 μM | 65% | 66% | 67% | 64% |
| 1.0 μM | 51% | 43% | 44% | 45% |
| 10 μM | 24% | 20% | 19% | 21% |

The results demonstrate that the capability of the water-soluble Dix-902, Dix-904 and Dix-906 in triggering dose-dependent cell death in H146 (small cell lung cancer) cells is similarly to or even slightly better than that of CPT.

Table 4 shows that compounds Dix-902, Dix-904and Dix-906 triggered dose-dependent cell death in MDAMB231 (breast cancer) cells. In the "CPT" group, the MDAMB231 (breast cancer) cells were treated with CPT (dissolved in DMSO) in 4 concentrations (0, 0.1, 1.0, 10 μM, respectively) for 48 hours. In the Dix-902, Dix-904 and Dix-906 groups, MDAMB231 (breast cancer) cells were treated respectively with the corresponding compounds (dissolved in a saline solution) in 4 concentrations (0, 0.1, 1.0, 10 μM, respectively) for 48 hours.

TABLE 4

MDAMB231 cell viability after 48 hours of treatment with CPT, Dix-902, Dix-904 and Dix-906.

| Conc. | Cell viability after treatment with CPT | Cell viability after treatment with Dix-902 | Cell viability after treatment with Dix-904 | Cell viability after treatment with Dix-906 |
|---|---|---|---|---|
| 0 μM | 100% | 100% | 100% | 100% |
| 0.1 μM | 13% | 15% | 13% | 14% |
| 1.0 μM | 5% | 4% | 3% | 4% |
| 10 μM | 3% | 2% | 1% | 3% |

The results demonstrate that the capability of the water-soluble Dix-902, Dix-904 and Dix-906 in triggering dose-dependent cell death in MDAMB231 (breast cancer) cells is similar to that of CPT.

Table 5 shows that Compounds Dix-902, Dix-904 and Dix-906 triggered dose-dependent cell death in HCT116 (colon cancer) cells. In the "CPT" group, the is HCT116 cells were treated with CPT (dissolved in DMSO) in 4 concentrations (0, 0.1, 1.0, 10 μM, respectively) for 48 hours. In the Dix-902, Dix-904 and Dix-906 groups, HCT116 cells were treated respectively with the corresponding compounds (dissolved in a saline solution) in 4 concentrations (0, 0.1, 1.0, 10 μM, respectively) for 48 hours.

TABLE 5

HCT116 cell viability after 48 hours of treatment with CPT, Dix-902, Dix-904 and Dix-906.

| Conc. | Cell viability after treatment with CPT | Cell viability after treatment with Dix-902 | Cell viability after treatment with Dix-904 | Cell viability after treatment with Dix-906 |
|---|---|---|---|---|
| 0 μM | 100% | 100% | 100% | 100% |
| 0.1 μM | 96% | 87% | 95% | 90% |
| 1.0 μM | 76% | 68% | 70% | 71% |
| 10 μM | 11% | 9% | 10% | 8% |

The results demonstrate that the effectiveness of the water-soluble Dix-902, Dix-904 and Dix-906 in triggering dose-dependent cell death in HCT116 (colon cancer) cells is higher than that CPT.

The foregoing description of the specific embodiments fully reveals the general nature of the invention that others can, by applying current knowledge, readily modify and/or adapt for various applications of such specific embodiments without departing from the generic concept, and therefore such adaptations and modifications are understood to be or are intended to be within the meaning and range of equivalents of the disclosed embodiments. It is to be understood that the phrases and terms employed herein are descriptive, rather than limiting.

What is claimed:

1. A water-soluble camptothecin derivative, comprising a compound of Formula I or a pharmaceutically acceptable salt thereof:

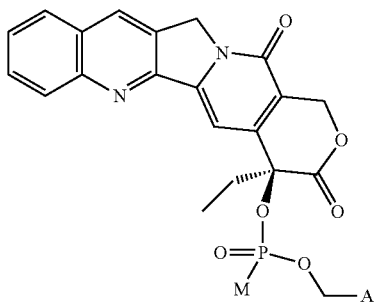

Formula I wherein M represents hydroxyl or thiol, A represents ribose or deoxyribose or ribose derivative and is attached to a phosphorus atom via an oxygen of an hydroxyl group.

2. The camptothecin derivative of claim 1, wherein A is a nucleoside or nucleoside analog wherein one or more hydrogen atoms in carbon-hydrogen bonds, nitrogen-hydrogen bonds, or hydroxyl group of a pentose and/or a nucleobase are substituted; or A is a nucleoside analog that contains a nucleobase derivative, wherein the nucleobase derivative is a heteroaryl or heteroalicyclic group other than adenine, thymine, cytosine or guanine, having 1 to 3 mono-cyclic rings and 1 to 3 N, O or S atoms.

3. A camptothecin derivative, comprising a chemical structure of Formula II:

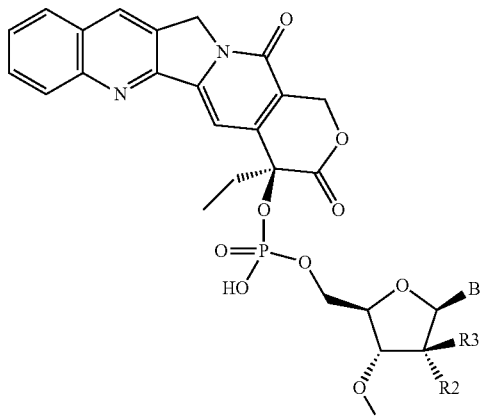

Formula II wherein R1 represents hydrogen, C1-C4 acyl, or an enzymatically reactive moiety;

R2 and R3 are the same or different, and independently represents hydrogen, halo, hydroxyl, alkoxy group, or an enzymatically reactive moiety;

B is hydrogen, optionally substituted thymine, optionally substituted adenine, optionally substituted cytosine, optionally substituted guanine, optionally substituted uracil, 5-fluorouricil, 5-aza-cytosine, 2-fluoroadenine, 2-chloroadenine, or 3,4,7,8-tetrahydroimidazo[1,3]-diazepin-8-ol; or B is a heteroaromatic or heteroalicyclic group other than adenine, thymidine, cytosine or guanine and preferably has from 1 to 3 mono-cyclic or fused-rings and 1 to 3 N, O or S atoms.

4. The camptothecin derivative of claim 3, wherein B is a substituted thymine, substituted adenine, substituted uracil, substituted cytosine, or substituted guanine, wherein the substitution group is alkyl, aryl, heteroaryl or heteroalicyclic group, wherein the heteroaryl or heteroalicyclic group has from 1 to 3 mono-cyclic or fused-rings and 1 to 3 N, O or S atoms.

5. The camptothecin derivative of claim 3, wherein R1 is C1-C4 acyl.

6. The camptothecin derivative of claim 5, wherein R1 is acetyl.

7. The camptothecin derivative of claim 3, wherein R1=R3=H, R2=OH, B=hydrogen, thymine, adenine, cytosine, guanine, uracil, or 5-aza-cytosine.

8. The camptothecin derivative of claim 3, wherein R1=Ac, R2=R3=H, B=hydrogen, thymine, adenine, cytosine, guanine, uracil, 5-aza-thymine, or 2-chloroadenine, wherein one hydrogen in an amino group is substituted with an acetyl group.

9. The camptothecin derivative of claim 3, wherein R1=Ac, R2=F, R3=H, B=2-chloroadenine, wherein one hydrogen of an amino group is substituted with acetyl.

10. The camptothecin derivative of claim 3, wherein R1=Ac, R2=H, R3=OAc, B=2-fluoadenine, wherein one hydrogen of an amino group is substituted with acetyl.

11. The camptothecin derivative of claim 3, wherein R1=Ac, R3=H, R2=OAc, B=hydrogen, thymine, adenine, cytosine, guanine, uracil, 5-aza-cytosine, wherein one hydrogen of an amino group is substituted with acetyl.

12. The camptothecin derivative of claim 3, wherein a combination of R1, R2, R3, and B is selected from a group consisted of combinations 1 to 21 listed in the following table 6:

| Combination # | R1 | R2 | R3 | B |
|---|---|---|---|---|
| 1 | H | H | H | 5-fluouracil |
| 2 | H | F | F | cytosine |
| 3 | H | H | H | 5-aza-cytosine |
| 4 | H | H | H | 2-chloroadenine |
| 5 | H | H | H | 3,4,7,8-tetrahydroimidazo[1,3]diazepin-8-ol |
| 6 | H | H | H | adenine |
| 7 | H | H | H | thymine |
| 8 | H | H | H | cytosine |
| 9 | H | H | H | guanine |
| 10 | H | H | H | H |
| 11 | H | H | H | uracil |
| 12 | H | H | H | 2-fluoroadenine |
| 13 | H | H | OH | 2-fluoroadenine |
| 14 | H | F | H | 2-chloroadenine |
| 15 | H | OH | H | thymine |
| 16 | H | OH | H | adenine |
| 17 | H | OH | H | cytosine |
| 18 | H | OH | H | guanine |

-continued

| Combination # | R1 | R2 | R3 | B |
|---|---|---|---|---|
| 19 | H | OH | H | H |
| 20 | H | OH | H | 5-aza-cytosine |
| 21 | Ac | H | H | 5-fluouracil. |

13. A method of preparing the compound of claim 3, comprising the following steps:

(1) reacting PCl$_3$ with an azole of RH, producing a phosphine triamine reagent of Formula IV:

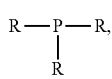

Formula IV wherein, R is

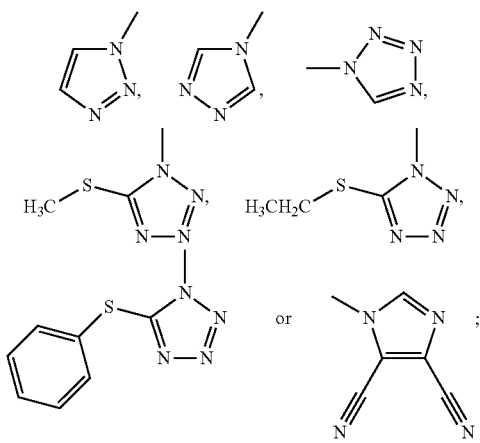

(2) reacting the phosphine triamine reagent of Formula IV with a CPT, producing a CPT 20(S)-O-phosphoramidite mono-ester intermediate of Formula V:

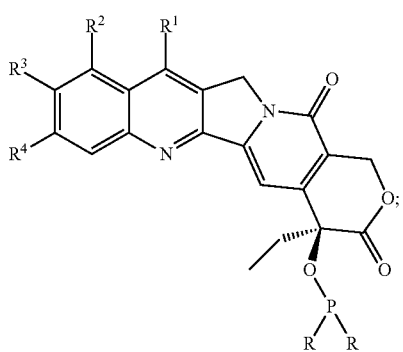

Formula V (3) reacting the CPT 20(S)-O-phosphoramidite intermediate of Formula V with the suitably protected compound of Formula III, producing 20(S)-O-phosphoramidite di-ester precursor of Formula VI:

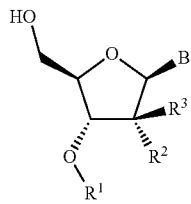

Formula III

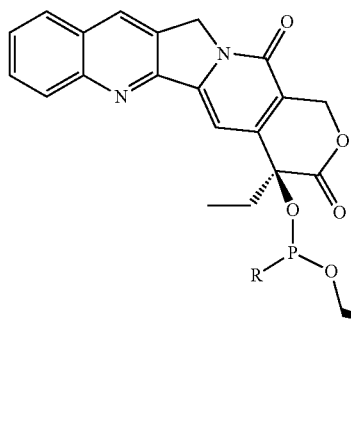

Formula VI wherein,
R1 represents H, C1-C4 acyl, or an enzymatically reactive moiety;
R2 and R3 are the same or different, and independently represents hydrogen, halo, hydroxyl, alkoxy, or an enzymatically reactive moiety;
B is hydrogen, an optionally substituted thymine, optionally substituted adenine, optionally substituted cytosine, optionally substituted guanine, optionally substituted uracil, 5-fluorouricil, 5-aza-cytosine, 2-fluoroadenine, 2-chloroadenine, or 3,4,7,8-tetrahydroimidazo[1,3]diazepin-8-ol; or a heteroaromatic or heteroalicyclic group other than adenine, thymidine, cytosine or guanine, and has from 1 to 3 mono- or fused-rings and 1 to 3 N, O or S atoms; and
(4) hydrolyzing the 20(S)-O-phosphoramidite di-ester precursor of Formula VI, followed by oxidation and ammonolysis to remove the protecting group, producing the CPT 20(S)-O-nucleotide CPT derivative of Formula II; and
(5) optionally, converting the compound of Formula II to a corresponding salt.

14. A pharmaceutical formulation, comprising at least one camptothecin derivative of claim 1 and a pharmaceutically acceptable carrier or diluent.

15. A method of treating a cancer, comprising
administrating to a subject an effective amount of the pharmaceutical composition according to claim 14 under conditions wherein the pharmaceutical composition inhibits, retards, and/or kills cancer cells in the subject;
wherein said cancer is selected from the group consisting of lung cancer, breast cancer, colon cancer, prostate cancer, melanoma, pancreas cancer, stomach cancer, liver cancer, brain cancer, kidney cancer, uterus cancer, cervix cancer, ovaries cancer, urinary track cancer, gastrointestinal cancer, leukemia, small cell lung cancer, solid tumor or blood borne tumor.

16. The method of claim 15, wherein said cancer is small cell lung cancer.

17. The method of claim 15, wherein said cancer is colon cancer.

18. The method of claim 13, wherein during step (3), R1 in the CPT 20(S)-O-phosphoramidite intermediate of Formula V is hydrogen, and the hydrogen is substituted with a suitable protecting group before reacting with the compound of Formula III.

19. The method of claim 13, wherein during step (3), R2 or R3 in the CPT 20(S)-O-phosphoramidite intermediate of Formula V is hydroxyl, and the hydroxyl group is suitably protected before reacting with the compound of Formula III.

20. The method of claim 13, wherein during step (3), B in the CPT 20(S)-O-phosphoramidite intermediate of Formula V contains amino, and the amino group is suitably protected before reacting with the compound of Formula III.

* * * * *